United States Patent
Baker et al.

(10) Patent No.: US 12,143,914 B2
(45) Date of Patent: Nov. 12, 2024

(54) DEVICE IDENTIFICATION METHOD

(71) Applicant: NICOVENTURES TRADING LIMITED, London (GB)

(72) Inventors: Darryl Baker, London (GB); Robert Kersey, London (GB); Patrick Moloney, London (GB)

(73) Assignee: NICOVENTURES TRADING LIMITED, London (GB)

( * ) Notice: Subject to any disclaimer, the term of this patent is extended or adjusted under 35 U.S.C. 154(b) by 0 days.

(21) Appl. No.: 18/322,834

(22) Filed: May 24, 2023

(65) Prior Publication Data

US 2023/0300586 A1    Sep. 21, 2023

Related U.S. Application Data

(63) Continuation of application No. 15/733,325, filed as application No. PCT/EP2018/086624 on Dec. 21, 2018, now Pat. No. 11,871,321.

(30) Foreign Application Priority Data

Dec. 29, 2017 (GB) ........................ 1722278

(51) Int. Cl.
 *H04W 4/80* (2018.01)
 *A24F 40/60* (2020.01)
 *A24F 40/65* (2020.01)

(52) U.S. Cl.
 CPC .............. *H04W 4/80* (2018.02); *A24F 40/60* (2020.01); *A24F 40/65* (2020.01)

(58) Field of Classification Search
 CPC . H04W 4/80; H04W 4/70; A24F 40/60; A24F 40/65; A61M 11/042; A61M 15/06; G06F 3/048; H04M 2201/42
(Continued)

(56) References Cited

U.S. PATENT DOCUMENTS 6,196,218 B1   3/2001 Voges
8,061,361 B2   11/2011 Maeder et al.
(Continued)

FOREIGN PATENT DOCUMENTS

CN   1631013 A   6/2005
CN   1633780 A   6/2005
(Continued)

OTHER PUBLICATIONS

Examination Report No. 1 received for Australian Patent Application No. 2021254534, mailed on Oct. 5, 2022, 3 Pages.
(Continued)

*Primary Examiner* — Eugene Yun
(74) *Attorney, Agent, or Firm* — BURR & FORMAN LLP

(57) ABSTRACT

The present disclosure teaches provision of a method and a portable electronic device. The method comprises receiving, via a wireless communication interface capable of supporting paired interaction, a data packet from an aerosol provision device via a wireless communication network. The data packet contains information relating to at least one physical characteristic of the aerosol provision device. An identity of the aerosol provision device is determined based at least in part on the at least one physical characteristic of the aerosol provision device and an aspect of a user interface is changed based on the determined identity of the aerosol provision device.

11 Claims, 11 Drawing Sheets

(58) Field of Classification Search
USPC .................................................. 455/41.2
See application file for complete search history.

(56) References Cited

U.S. PATENT DOCUMENTS

| | | | |
|---|---|---|---|
| 9,254,007 B2 | 2/2016 | Liu | |
| 9,642,167 B1 | 5/2017 | Snyder et al. | |
| 10,097,387 B1 | 10/2018 | Wiser et al. | |
| 10,258,087 B2 | 4/2019 | Kane | |
| 10,349,675 B2 | 7/2019 | Choukroun et al. | |
| 11,213,638 B2 | 1/2022 | Nettenstrom et al. | |
| 11,388,931 B2 | 7/2022 | Potter et al. | |
| 11,510,040 B2 | 11/2022 | Kersey et al. | |
| 2004/0047319 A1 | 3/2004 | Elg | |
| 2005/0117066 A1 | 6/2005 | Kamijo | |
| 2011/0005535 A1 | 1/2011 | Xiu | |
| 2011/0021142 A1 | 1/2011 | Desai et al. | |
| 2011/0265806 A1 | 11/2011 | Alarcon et al. | |
| 2012/0196534 A1 | 8/2012 | Kasslin et al. | |
| 2013/0065584 A1 | 3/2013 | Lyon et al. | |
| 2013/0081642 A1 | 4/2013 | Safari | |
| 2013/0087160 A1 | 4/2013 | Gherghe | |
| 2013/0178160 A1 | 7/2013 | Wang | |
| 2013/0228191 A1 | 9/2013 | Newton | |
| 2013/0263869 A1 | 10/2013 | Zhu | |
| 2013/0276799 A1 | 10/2013 | Davidson et al. | |
| 2013/0284192 A1 | 10/2013 | Peleg et al. | |
| 2013/0306065 A1 | 11/2013 | Thorens et al. | |
| 2013/0340775 A1 | 12/2013 | Juster et al. | |
| 2014/0020697 A1 | 1/2014 | Liu | |
| 2014/0060528 A1 | 3/2014 | Liu | |
| 2014/0107815 A1 | 4/2014 | Lamothe | |
| 2014/0123989 A1 | 5/2014 | Lamothe | |
| 2014/0130816 A1 | 5/2014 | Liu | |
| 2014/0169599 A1 | 6/2014 | Solum et al. | |
| 2014/0174459 A1 | 6/2014 | Burstyn | |
| 2014/0202477 A1 | 7/2014 | Qi et al. | |
| 2014/0238423 A1 | 8/2014 | Tucker et al. | |
| 2014/0238424 A1 | 8/2014 | Macko et al. | |
| 2014/0278250 A1 | 9/2014 | Smith et al. | |
| 2014/0351721 A1 | 11/2014 | Deluca et al. | |
| 2014/0378057 A1 | 12/2014 | Ramon et al. | |
| 2014/0378790 A1 | 12/2014 | Cohen | |
| 2015/0040927 A1 | 2/2015 | Li et al. | |
| 2015/0099469 A1 | 4/2015 | Goldstein | |
| 2015/0101625 A1* | 4/2015 | Newton | A24F 40/60 131/329 |
| 2015/0101940 A1 | 4/2015 | Ash | |
| 2015/0133054 A1 | 5/2015 | Chen et al. | |
| 2015/0134619 A1 | 5/2015 | Factor et al. | |
| 2015/0142387 A1 | 5/2015 | Alarcon et al. | |
| 2015/0144145 A1 | 5/2015 | Chang et al. | |
| 2015/0172391 A1 | 6/2015 | Kasslin et al. | |
| 2015/0216237 A1 | 8/2015 | Wensley et al. | |
| 2015/0224268 A1 | 8/2015 | Henry et al. | |
| 2015/0272220 A1 | 10/2015 | Spinka et al. | |
| 2015/0312858 A1 | 10/2015 | Kerai | |
| 2015/0313283 A1 | 11/2015 | Collett et al. | |
| 2015/0319555 A1 | 11/2015 | Cordeiro et al. | |
| 2015/0327596 A1 | 11/2015 | Alarcon et al. | |
| 2015/0358759 A1 | 12/2015 | Jakusovszky et al. | |
| 2016/0015081 A1 | 1/2016 | Liu | |
| 2016/0015082 A1 | 1/2016 | Liu | |
| 2016/0021488 A1 | 1/2016 | Viswanadham et al. | |
| 2016/0029148 A1 | 1/2016 | Jackson et al. | |
| 2016/0029149 A1 | 1/2016 | Morikawa et al. | |
| 2016/0037012 A1 | 2/2016 | Okado | |
| 2016/0037566 A1 | 2/2016 | Jakusovszky et al. | |
| 2016/0073692 A1 | 3/2016 | Alarcon et al. | |
| 2016/0089508 A1 | 3/2016 | Smith et al. | |
| 2016/0100276 A1 | 4/2016 | Viswanadham et al. | |
| 2016/0100311 A1 | 4/2016 | Kumar | |
| 2016/0105761 A1 | 4/2016 | Polo et al. | |
| 2016/0121058 A1 | 5/2016 | Chen | |
| 2016/0184635 A1 | 6/2016 | Kwon | |
| 2016/0191642 A1 | 6/2016 | Acar | |
| 2016/0262451 A1 | 9/2016 | Liu | |
| 2016/0278163 A1 | 9/2016 | Chen | |
| 2016/0278435 A1 | 9/2016 | Choukroun et al. | |
| 2016/0286863 A1 | 10/2016 | Lin | |
| 2016/0316819 A1 | 11/2016 | Zhou et al. | |
| 2016/0338407 A1 | 11/2016 | Kerdemelidis | |
| 2016/0345632 A1 | 12/2016 | Lipowicz | |
| 2016/0353798 A1 | 12/2016 | Liu | |
| 2016/0353800 A1 | 12/2016 | Di Carlo | |
| 2016/0363570 A1 | 12/2016 | Blackley | |
| 2016/0363917 A1 | 12/2016 | Blackley | |
| 2016/0374133 A1 | 12/2016 | Logue et al. | |
| 2017/0020188 A1* | 1/2017 | Cameron | A24F 40/60 |
| 2017/0026905 A1 | 1/2017 | Denboer et al. | |
| 2017/0041381 A1 | 2/2017 | Tal et al. | |
| 2017/0041868 A1 | 2/2017 | Palin et al. | |
| 2017/0042242 A1 | 2/2017 | Hon | |
| 2017/0071262 A1 | 3/2017 | Liu | |
| 2017/0093960 A1 | 3/2017 | Cameron | |
| 2017/0093981 A1 | 3/2017 | Cameron | |
| 2017/0118292 A1 | 4/2017 | Xiang | |
| 2017/0127725 A1 | 5/2017 | Buchberger et al. | |
| 2017/0193816 A1 | 7/2017 | Lee et al. | |
| 2017/0223604 A1 | 8/2017 | Skillermark et al. | |
| 2017/0258136 A1* | 9/2017 | Hawes | A24F 40/53 |
| 2017/0273358 A1 | 9/2017 | Batista et al. | |
| 2017/0273359 A1 | 9/2017 | Liu | |
| 2017/0303596 A1 | 10/2017 | Chen | |
| 2018/0062868 A1 | 3/2018 | Higo et al. | |
| 2018/0132102 A1 | 5/2018 | Kwon et al. | |
| 2018/0270311 A1 | 9/2018 | Baker et al. | |
| 2018/0270643 A1 | 9/2018 | Baker et al. | |
| 2018/0280640 A1 | 10/2018 | Baker et al. | |
| 2018/0286208 A1 | 10/2018 | Baker et al. | |
| 2018/0303163 A1 | 10/2018 | Baker et al. | |
| 2019/0286456 A1 | 9/2019 | Baker et al. | |
| 2020/0029371 A1 | 1/2020 | Achtien et al. | |
| 2020/0060347 A1 | 2/2020 | Kersey et al. | |
| 2020/0178607 A1 | 6/2020 | Blick et al. | |
| 2020/0237014 A1* | 7/2020 | Lee | A61M 15/06 |
| 2020/0315254 A1 | 10/2020 | Zielazek et al. | |
| 2020/0323275 A1* | 10/2020 | Baker | A24F 40/65 |
| 2020/0329356 A1 | 10/2020 | Moloney et al. | |
| 2020/0352238 A1 | 11/2020 | Simpson et al. | |
| 2021/0145055 A1 | 5/2021 | Potter et al. | |
| 2021/0251300 A1 | 8/2021 | Jung et al. | |
| 2021/0308392 A1 | 10/2021 | Alarcon et al. | |
| 2022/0060873 A1 | 2/2022 | Kersey et al. | |
| 2022/0095688 A1 | 3/2022 | Talbot et al. | |

FOREIGN PATENT DOCUMENTS

| | | |
|---|---|---|
| CN | 101800575 A | 8/2010 |
| CN | 102035574 A | 4/2011 |
| CN | 201781984 U | 4/2011 |
| CN | 201830900 U | 5/2011 |
| CN | 102684753 A | 9/2012 |
| CN | 102970885 A | 3/2013 |
| CN | 103380952 A | 11/2013 |
| CN | 103798960 A | 5/2014 |
| CN | 103914013 A | 7/2014 |
| CN | 203913385 U | 11/2014 |
| CN | 204120237 U | 1/2015 |
| CN | 104366695 A | 2/2015 |
| CN | 104412629 A | 3/2015 |
| CN | 104488348 A | 4/2015 |
| CN | 204351068 U | 5/2015 |
| CN | 104664605 A | 6/2015 |
| CN | 104720117 A | 6/2015 |
| CN | 104811895 A | 7/2015 |
| CN | 204426699 U | 7/2015 |
| CN | 204483034 U | 7/2015 |
| CN | 204483035 U | 7/2015 |
| CN | 104955508 A | 9/2015 |
| CN | 104980284 A | 10/2015 |
| CN | 105163614 A | 12/2015 |
| CN | 105188428 A | 12/2015 |
| CN | 105208882 A | 12/2015 |

(56) References Cited

FOREIGN PATENT DOCUMENTS

| | | |
|---|---|---|
| CN | 105210420 A | 12/2015 |
| CN | 105310114 A | 2/2016 |
| CN | 105342010 A | 2/2016 |
| CN | 105433442 A | 3/2016 |
| CN | 205285008 U | 6/2016 |
| CN | 205512338 U | 8/2016 |
| CN | 205624465 U | 10/2016 |
| CN | 106102811 A | 11/2016 |
| CN | 106376976 A | 2/2017 |
| CN | 106535682 A | 3/2017 |
| CN | 106604655 A | 4/2017 |
| CN | 206119177 U | 4/2017 |
| CN | 206197019 U | 5/2017 |
| CN | 206197020 U | 5/2017 |
| CN | 107251583 A | 10/2017 |
| CN | 107301020 A | 10/2017 |
| CN | 107708452 A | 2/2018 |
| CN | 108028859 A | 5/2018 |
| CN | 108968167 A | 12/2018 |
| EP | 1357712 A1 | 10/2003 |
| EP | 1494403 A3 | 9/2009 |
| EP | 2110034 A1 | 10/2009 |
| EP | 2460424 A1 | 6/2012 |
| EP | 2533477 A1 | 12/2012 |
| EP | 2533477 B1 | 3/2014 |
| EP | 2739020 A2 | 6/2014 |
| EP | 2823720 A1 | 1/2015 |
| EP | 2959784 A1 | 12/2015 |
| EP | 2984952 A1 | 2/2016 |
| EP | 3062643 A1 | 9/2016 |
| EP | 3108759 A1 | 12/2016 |
| GB | 2513639 A | 11/2014 |
| GB | 2521224 A | 6/2015 |
| JP | 2001352377 A | 12/2001 |
| JP | 2002044730 A | 2/2002 |
| JP | 2002247097 A | 8/2002 |
| JP | 2002252616 A | 9/2002 |
| JP | 2003229782 A | 8/2003 |
| JP | 2005159821 A | 6/2005 |
| JP | 2005236819 A | 9/2005 |
| JP | 2007036421 A | 2/2007 |
| JP | 2009252002 A | 10/2009 |
| JP | 2013524835 A | 6/2013 |
| JP | 2014110635 A | 6/2014 |
| JP | 2014110637 A | 6/2014 |
| JP | 2015180214 A | 10/2015 |
| JP | 2017076870 A | 4/2017 |
| JP | 2017514504 A | 6/2017 |
| JP | 2017169185 A | 9/2017 |
| JP | 2018032269 A | 3/2018 |
| JP | 2018533924 A | 11/2018 |
| JP | 2018536309 A | 12/2018 |
| JP | 2020526222 A | 8/2020 |
| JP | 2021506296 A | 2/2021 |
| JP | 2021048589 A | 3/2021 |
| JP | 2021523685 A | 9/2021 |
| KR | 20020057207 A | 7/2002 |
| KR | 20120098343 A | 9/2012 |
| KR | 20140002774 U | 5/2014 |
| KR | 20150032188 A | 3/2015 |
| KR | 101570106 B1 | 11/2015 |
| KR | 20150140584 A | 12/2015 |
| KR | 20160009678 A | 1/2016 |
| KR | 101609715 B1 | 4/2016 |
| RU | 2420901 C2 | 6/2011 |
| RU | 2425608 C2 | 8/2011 |
| RU | 2011120430 A | 11/2012 |
| RU | 2509516 C2 | 3/2014 |
| RU | 2536166 C2 | 12/2014 |
| RU | 161240 U1 | 4/2016 |
| RU | 2598568 C2 | 9/2016 |
| RU | 2606572 C2 | 1/2017 |
| RU | 2620754 C2 | 5/2017 |
| RU | 2636917 C2 | 11/2017 |
| RU | 2638917 C2 | 12/2017 |
| RU | 2639972 C2 | 12/2017 |
| TW | 201513524 A | 4/2015 |
| TW | 201613524 A | 4/2016 |
| WO | 2005057956 A1 | 6/2005 |
| WO | 2011137453 A2 | 11/2011 |
| WO | 2011146375 A2 | 11/2011 |
| WO | 2014045155 A1 | 3/2014 |
| WO | 2014060269 A1 | 4/2014 |
| WO | 2014085719 A1 | 6/2014 |
| WO | 2014088230 A1 | 6/2014 |
| WO | 2014150704 A2 | 9/2014 |
| WO | 2014195805 A2 | 12/2014 |
| WO | 2015063126 A1 | 5/2015 |
| WO | 2015099751 A1 | 7/2015 |
| WO | 2016017909 A1 | 2/2016 |
| WO | 2016037012 A1 | 3/2016 |
| WO | 2016041209 A1 | 3/2016 |
| WO | 2016079151 A1 | 5/2016 |
| WO | 2016090531 A1 | 6/2016 |
| WO | 2016108646 A1 | 7/2016 |
| WO | 2016176800 A1 | 11/2016 |
| WO | 2016179271 A1 | 11/2016 |
| WO | 2016190222 A1 | 12/2016 |
| WO | 2016198417 A1 | 12/2016 |
| WO | 2016207357 A1 | 12/2016 |
| WO | 2016208756 A1 | 12/2016 |
| WO | 2017001818 A1 | 1/2017 |
| WO | 2017001819 A1 | 1/2017 |
| WO | 2017015832 A1 | 2/2017 |
| WO | 2017020188 A1 | 2/2017 |
| WO | 2017051173 A1 | 3/2017 |
| WO | 2017051174 A1 | 3/2017 |
| WO | 2017055795 A1 | 4/2017 |
| WO | 2017055800 A1 | 4/2017 |
| WO | 2017055801 A1 | 4/2017 |
| WO | 2017055802 A1 | 4/2017 |
| WO | 2017203488 A1 | 11/2017 |
| WO | 2017215221 A1 | 12/2017 |
| WO | 2018202651 A1 | 11/2018 |
| WO | 2019121778 A1 | 6/2019 |

OTHER PUBLICATIONS

Notice of Allowance received for Korean Patent Application No. 10-2022-7001663, mailed on Feb. 16, 2023, 6 pages (3 pages of English Translation and 3 pages of Official Copy).
Notice of Allowance received for Korean Patent Application No. 10-2022-7001975, mailed on Feb. 16, 2023, 4 pages (1 page of English Translation and 3 pages of Official Copy).
Notice of Reasons for Rejection received for Japanese Patent Application No. 2021-148436, mailed on Nov. 29, 2022, 8 pages (4 pages of English Translation and 4 pages of Official Copy).
Office Action and Search Report received for Chinese Application No. 2018800844162, mailed Dec. 22, 2022, 17 pages (8 pages of English Translation and 9 pages of Official Copy).
Office Action received for Russian Patent Application No. 2022114546, mailed on Nov. 18, 2022, 6 pages (Official Copy Only).
Otiaba , et al., Application and File History for U.S. Appl. No. 16/610,588, filed Nov. 4, 2019, 242 Pages.
Chinese Office Action, Application No. 201680047153.9, dated Nov. 21, 2019, 12 Pages.
Decision of grant for Russian Application No. 2019134027 mailed on Aug. 18, 2020, 10 Pages.
European Office Action, Application No. 16775827.5, dated Jan. 28, 2019, 5 Pages.
Examination Report No. 1 mailed Jun. 1, 2021 for New Zealand Application No. 765016, 4 Pages.
Extended European Search Report for Application No. 20204701.5, mailed on Jan. 28, 2021, 8 Pages.
Extended European Search Report for Application No. 21201390.8, mailed on Jan. 28, 2022, 9 Pages.
Great Britain Search Report, Application No. GB 1516674.7, dated Feb. 18, 2016, 5 Pages.
"IEEE 802.15 WPAN Task Group 1 (TGI)", IEEE 802.15 as retrieved on Mar. 15, 2016., 2 Pages.

(56) References Cited

OTHER PUBLICATIONS

"IEEE Standard", IEEE 802.11 as retrieved on Feb. 19, 2018, 2 Pages.
"IEEE Standard for Local Metropolitan Area Networks, Part 15.4: Low-Rate Wireless Personal Area Networks (LR-WPANs)", IEEE Std 802.15.4, Sep. 5, 2011, 314 Pages.
International Preliminary Report on Patentability for Application No. PCT/EP2018/061086, mailed on Oct. 10, 2019, 15 Pages.
International Preliminary Report on Patentability for Application No. PCT/EP2018/086624, mailed Mar. 16, 2020, 15 Pages.
International Preliminary Report on Patentability for Application No. PCT/GB2016/052939, mailed on Sep. 14, 2017, 9 Pages.
International Preliminary Report on Patentability, for Application No. PCT/EP2018/086791, mailed Mar. 12, 2020, 13 Pages.
International Preliminary Report on Patentability, International Application No. PCT/GB2016/052940, mailed Sep. 14, 2017, 8 Pages.
International Search Report and Written Opinion for Application No. PCT/EP2018/086624, mailed Feb. 11, 2019, 13 Pages.
International Search Report and Written Opinion received for PCT Patent Application No. PCT/GB2016/052939, mailed on Nov. 18, 2016, 17 Pages.
International Search Report and Written Opinion received for PCT patent Application No. PCT/EP2018/061086, mailed on Jul. 11, 2018, 14 Pages.
International Search Report and Written Opinion, for Application No. PCT/EP2018/086791, mailed Feb. 13, 2019, 14 Pages.
International Search Report and Written Opinion, International Application No. PCT/GB2016/052940, mailed Dec. 8, 2016, 12 Pages.
Japanese Office Action, Application No. 2018-513274, dated Jan. 31, 2019, 4 pages.
Japanese Office Action, Application No. 2018-513357, dated Jan. 29, 2019, 7 pages.
Notice of Reasons for Refusal mailed Nov. 24, 2021 for Japanese Application No. 2020-183041, 8 pages.
Office Action For Chinese Application No. 201880029165.8, mailed on Mar. 16, 2022, 16 Pages.
Office Action For Japanese Application No. 2020-530641, mailed on Aug. 17, 2021, 5 Pages.
Office Action For Japanese Application No. 2020-531510, mailed on Sep. 21, 2021, 5 Pages.
Office action for Japanese Application No. 2021-169568, mailed on Aug. 23, 2022, 16 pages.
Office action for Korean Application No. 10-2022-7001663, mailed on Aug. 10, 2022, 12 pages.
Office Action For Russian Application No. 2020120938, mailed on Nov. 11, 2020, 13 Pages.
Office Action for Russian Application No. 2020121494, mailed on Nov. 18, 2020, 6 Pages.
Office Action for Russian Application No. 2020135708, mailed on May 24, 2021, 16 Pages.
Office Action mailed May 11, 2022 for Russian Application No. 2021132532, 12 pages.
Office Action mailed Nov. 15, 2021 for Japanese Application No. 2020-183041, 42 pages.
Office Action mailed Apr. 21, 2021 for Korean Application No. 10-2020-7018465, 11 Pages.
Office Action mailed Jul. 30, 2020 for Korean Application No. 10-2019-7032414 filed Oct. 31, 2019, 11 Pages.
Partial Search Report received for Great Britain Patent Application No. GB1516673.9, mailed on Feb. 18, 2016, 4 Pages.
Russian Decision to Grant, Application No. 2018109578/08, dated Apr. 3, 2019, 12 Pages.
Russian Decision to Grant, Application No. 2018109786/08, dated Dec. 13, 2018, 10 Pages.
Russian Search Report, Application No. 2018109786/08, dated Dec. 13, 2018, 2 Pages.
Second Written Opinion received for PCT patent Application No. PCT/EP2018/061086, mailed on Jul. 23, 2019, 8 Pages.
Written Opinion of International Preliminary Authority for Application No. PCT/EP2018/086624, mailed Nov. 25, 2019, 6 Pages.
Written Opinion received for PCT patent Application No. PCT/EP2018/061086, mailed on Apr. 10, 2019, 8 Pages.
Baker, Darryl, et al., Application and File History for U.S. Appl. No. 15/733,325, filed Jun. 26, 2020.
Baker, Application and File History for U.S. Appl. No. 15/762,018, filed Mar. 21, 2018, 446 Pages.
Baker, Application and File History for U.S. Appl. No. 15/762,021, filed Mar. 21, 2018, 442 Pages.
Bluetooth, "Specification of the Bluetooth System: Experience More", Covered Core Package version: 4.0, Specification vol. 1, Jun. 30, 2010, 137 Pages.
Bronzi, W, et al., "Bluetooth Low Energy for Inter-Vehicular Communications", 2014 IEEE Vehicular Networking Conference (VNC) IEEE, Dec. 3, 2014, pp. 215-221.
Moloney, Patrick, et al., Application and File History for U.S. Appl. No. 15/733,324, filed Jun. 26, 2020.
Moloney, Patrick, et al., Application and File History for U.S. Appl. No. 16/610,587, filed Nov. 4, 2019.
Yong, Liu, et al., "A Bluetooth Scatternet-Route Structure for Multihop Ad Hoc Networks", IEEE Journal on Selected Areas in Communications, vol. 21, No. 2, Feb. 1, 2003, pp. 229-239.
Notice of Allowance (with translation) issued in corresponding Japanese Application No. 2021-148436 on May 18, 2023, all enclosed pages cited.
Extended European Search Report issued in corresponding European Application No. 23204201.0 on Feb. 6, 2024, all enclosed pages cited.
Office Action issued in Canadian Application No. 3,170,619 on Dec. 20, 2023, all enclosed pages cited.
"Communication pursuant to Article 94(3) EPC for European Patent Application No. 18715070.1, mailed on Aug. 4, 2022", 6 pages.
"Communication pursuant to Article 94(3) EPC for European Patent Application No. 18715070.1, mailed on Nov. 2, 2020", 21 pages.
"Decision to Grant received for Japanese Patent Application No. 2020-537201, mailed on Jul. 13, 2021", 5 pages (2 pages of English Translation and 3 pages Official Copy).
"International Preliminary Report on Patentability received for PCT Patent Application No. PCT/GB2018/050726, mailed on Jul. 3, 2019", 32 pages.
"International Preliminary Report on Patentability received for PCT Patent Application No. PCT/GB2019/050037, mailed on May 8, 2020", 21 pages.
"International Preliminary Report on Patentability received for PCT Patent Application No. PCT/GB2019/050186, mailed on May 8, 2020", 8 pages.
"International Preliminary Report on Patentability received for PCT Patent Application No. PCT/GB2019/050187, mailed on Aug. 6, 2020,", 8 pages.
"International Search Report and Written Opinion received for PCT Patent Application No. PCT/GB2018/050726, mailed on Jun. 12, 2018", 15 pages.
"International Search Report and Written Opinion received for PCT Patent Application No. PCT/GB2019/050037, mailed on Mar. 25, 2019", 12 pages.
"International Search Report and Written Opinion received for PCT Patent Application No. PCT/GB2019/050089, mailed on Mar. 25, 2019", 14 pages.
"International Search Report received for PCT Patent Application No. PCT/GB2019/050187, mailed on Apr. 18, 2019", 3 pages.
"Notice of Allowance received for Korean Patent Application No. 10-2020-7021264, mailed on Nov. 14, 2022", 6 pages (3 pages of English Translation and 3 pages of Official Copy).
"Office Action received for Canadian Patent Application No. 3089292, mailed on Dec. 16, 2021", 6 pages.
"Office Action received for Chinese Patent Application No. 201880020522.4, mailed on Aug. 3, 2021", 14 pages (Official Copy Only).
"Office Action received for Chinese Patent Application No. 201880020522.4, mailed on May 20, 2022", 12 pages (10 pages of English Translation and 2 pages of Official Copy).

(56) References Cited

OTHER PUBLICATIONS

"Office Action received for Chinese Patent Application No. 201980009907.5, mailed on Nov. 2, 2022", 17 pages (9 pages of English Translation and 8 pages of Official Copy).
"Office Action received for Russian Patent Application No. 2020124567, mailed on Jan. 28, 2021", 2 pages (Official Copy Only).
"Reason of Refusal received for Korean Patent Application No. 10-2019-7027899, mailed on Jan. 18, 2021", 17 pages (9 pages of English Translation and 8 pages of Official Copy).
"Reasons for Refusal received for Korean Patent Application No. 10-2019-7027899, mailed on Jul. 27, 2021", 15 pages (8 pages of English Translation and 7 pages of Official Copy).
"Reasons for Rejection received for Japanese Patent Application No. 2020-539826, mailed on Jun. 15, 2021", 14 pages (7 pages of English Translation and 7 pages of Official Copy).
"Search Report received for Great Britain Patent Application No. GB 1702861.4, mailed on May 31, 2017", 5 pages.
"Search Report received for Great Britain Patent Application No. GB 1704674.9, mailed on Apr. 27, 2017", 5 pages.
"Search Report received for Russian Patent Application No. 2020124379, mailed on Mar. 2, 2021", 2 pages (Official Copy Only).
"Second Office Action received for Chinese Patent Application No. 201880020522.4, mailed on Jan. 20, 2022", 17 pages (7 pages of English Translation and 10 pages of Official Copy).
Vaporesso, "What's the Difference Between an Atomizer, Cartomizer and Clearomizer?", Available at <https://www.vaporesso.com/blog/difference-between-an-atomizer-cartomizer-and-clearomizer>, Aug. 7, 2019, 6 pages.

\* cited by examiner

```
                           Start
                             │
                             ▼                                    ─ S16-1
┌─────────────────────────────────────────────────────────────┐
│ Receive a data packet from a first aerosol provision device │
│ via a wireless communication network, wherein the data      │
│ packet contains information relating to at least one        │
│ physical characteristic of the aerosol provision device     │
└─────────────────────────────────────────────────────────────┘
                             │                                    ─ S16-2
                             ▼
┌─────────────────────────────────────────────────────────────┐
│ Receive a data packet from a second aerosol provision       │
│ device via a wireless communication network, wherein the    │
│ data packet contains information relating to at least one   │
│ physical characteristic of the second aerosol provision     │
│ device                                                      │
└─────────────────────────────────────────────────────────────┘
                             │                                    ─ S16-3
                             ▼
┌─────────────────────────────────────────────────────────────┐
│ Determine the identity of the first second aerosol          │
│ provision device based at least in part on the at least     │
│ one physical characteristic of the first aerosol provision  │
│ device                                                      │
└─────────────────────────────────────────────────────────────┘
                             │                                    ─ S16-4
                             ▼
┌─────────────────────────────────────────────────────────────┐
│ Determine the identity of the second aerosol provision      │
│ device based at least in part on the at least one physical  │
│ characteristic of the second aerosol provision device       │
└─────────────────────────────────────────────────────────────┘
                             │                                    ─ S16-5
                             ▼
┌─────────────────────────────────────────────────────────────┐
│ Change an aspect of a user interface based on the           │
│ determined identity of the first and second aerosol         │
│ provision device such as to enable a selection from a user  │
│ of one of the first or second aerosol provision devices.    │
└─────────────────────────────────────────────────────────────┘
                             │
                             ▼
                           Stop
```

FIG. 16

DEVICE IDENTIFICATION METHOD

PRIORITY CLAIM

The present application is a Continuation of application Ser. No. 15/733,325, filed on Jun. 26, 2020, which is a National Phase entry of PCT Application No. PCT/EP2018/086624, filed Dec. 21, 2018, which claims priority from GB Patent Application No. 1722278.7, filed Dec. 29, 2017, each of which is hereby fully incorporated herein by reference.

TECHNICAL FIELD

The present disclosure relates to a method and a portable electronic device.

BACKGROUND

In conventional wireless communication approaches, such as Bluetooth and Bluetooth Low Energy (also known as Bluetooth Smart Technology), individual devices can be operated as nodes taking the role of masters or slaves in a particular communication relationship. Thus each node adopts the role of master or the role of slave. Accordingly, in a communication pair, one node acts as master and the other acts as slave. In the context of Bluetooth Low Energy, the master may be referred to as the central and the slave as the peripheral. One master (or central) node can be a master to several slaves (the exact number often limited by a particular chipset implementation) and although a node can be registered as a slave (or peripheral) to multiple masters, it can only be active as a slave to one master at any one time.

Bluetooth and Bluetooth Low Energy are fundamentally different in operation to other Low-rate wireless personal area networks (LR-WPANs) such as Zigbee™ and Thread™, which are both based upon the IEEE 802.15.4 wireless protocol.

Publications WO 2017/020188 and US 2014/0107815 described examples of exchanging information between an aerosol provision device and another electronic device.

SUMMARY

Some specific aspects and embodiments are set out in the appended claims.

Viewed from a first aspect, there can be provided a method comprising: receiving, via a wireless communication interface capable of supporting paired interaction, a data packet from an aerosol provision device via a wireless communication network, wherein the data packet contains information relating to at least one physical characteristic of the aerosol provision device; determining the identity of the aerosol provision device based at least in part on the at least one physical characteristic of the aerosol provision device; and changing an aspect of a user interface based on the determined identity of the aerosol provision device.

Viewed from another aspect, there can be provided a portable electronic device comprising: at least one processor; a display; a wireless communication interface capable of supporting paired interaction; memory comprising instructions which, when executed by the at least one processor cause the at least one processor to: receive, via the Bluetooth low energy communication interface, a data packet from an aerosol provision device, wherein the data packet contains information relating to at least one physical characteristic of the aerosol provision device; determine, based at least in part on the at physical characteristic of the aerosol provision device, the identity of the aerosol provision device; and change an aspect of a user interface displayed on the display to be changed based on the determined identity of the aerosol provision device.

BRIEF DESCRIPTION OF THE DRAWINGS

Embodiments of the present teachings will now be described, by way of example only, with reference to accompanying drawings, in which:

FIG. 16 illustrates a further method for a portable electronic device.

Figure 1:
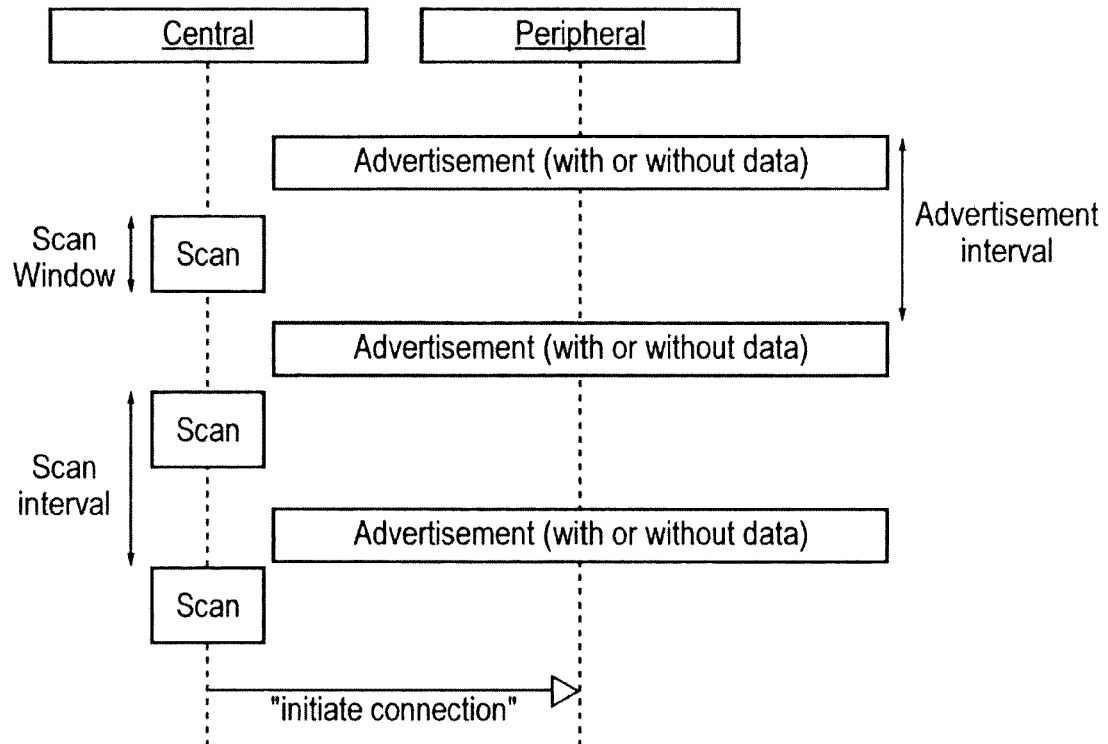
FIG. 1 schematically illustrates an advertising protocol.

While the presently described approach is susceptible to various modifications and alternative forms, specific embodiments are shown by way of example in the drawings and are herein described in detail. It should be understood, however, that drawings and detailed description thereto are not intended to limit the scope to the particular form disclosed, but on the contrary, the scope is to cover all modifications, equivalents and alternatives falling within the spirit and scope as defined by the appended claims.

DETAILED DESCRIPTION

The present disclosure relates to a modified form of wireless communication behavior. According to the present teachings, a device can be configured to use a Bluetooth or Bluetooth-like communications protocol and can, in a manner that may be transparent to other devices using the communications protocol for communication with the device, operate as both a master/central and a slave/peripheral in different communication relationships at the same time on a time division basis.

In some examples, the devices can be aerosol provision devices such as so-called "E-cigarettes", sometimes also known as Electronic Nicotine Delivery devices (END devices), provided with electronics that allow them to communicate with other communication devices. As used herein, the term "aerosol provision device" refers either to a device including an aerosol source material (e.g., a device part and a disposable cartomizer part containing the aerosol source material) and/or a device not including an aerosol source material (e.g., just the device part of the previous example).

In the present examples, the devices use Bluetooth Low Energy ("BTLE"), but other Bluetooth protocols or Bluetooth-like protocols can take advantage of the present teachings. Bluetooth is a wireless technology standard for short distance communication between appropriately enabled devices. BTLE is a variant on the original Bluetooth system, designed to draw less power in use for extended battery life and/or small battery applications. Both Bluetooth and BTLE operate in the UHF radio industrial, scientific and medical (ISM) band from 2.4 to 2.485 GHz and are designed for creating so-called wireless personal area networks (PANs) for interconnecting devices over short distances. BTLE uses a modified version of the Bluetooth stack for communication such that a BTLE device and a traditional Bluetooth device are not directly compatible unless one device implements both protocols. Both Bluetooth and BTLE standards are maintained by the Bluetooth Special Interest Group (SIG). The present disclosure is provided in the context of a BTLE implementation using the part of the Bluetooth v4 specification that relates to BTLE. However, the skilled reader will appreciate that the present teachings can be applied to other Bluetooth approaches, such as the so-called Classic Bluetooth definitions that are also set out in the Bluetooth v4 specification. It will be further appreciated that the present teachings can be applied to technologies that are not in accordance with an entire Bluetooth specification, but which nevertheless behave in a Bluetooth-like manner.

For example, non-Bluetooth systems that nevertheless use an advertising setup based on the Bluetooth Low Energy Generic Access Profile (GAP) and thus have an advertising structure substantially as set out in FIG. 1 would be able to deploy the techniques of the present teachings. FIG. 1 illustrates an advertising structure according to which a peripheral (or slave or remote or secondary) device advertises its availability as a peripheral (or slave or remote or secondary) device during an advertisement period, with the advertisement periods being separated by an advertisement interval. The advertisement may include data for transmission, an indication that there is data for transmission or have no data reference at all. To receive the advertisement, a central (or primary or control) device scans for advertisements during a scan window. Multiple scan windows are separated by a scan interval. The relative duration of the scan and advertisement intervals is altered, either by determining that the interval at one device type is constant while the other varies, or by determining that both vary, which determination can be set by a standard or rule set for implementing the advertising protocol. By providing this relative variation in the scan and advertisement intervals, it is provided that even where an initial advertisement period does not overlap with an initial scan window, after a number of advertisement and scan intervals, an advertisement period will occur which overlaps with a scan window such that a connection can be initiated between the central and the peripheral device.

Figure 2:
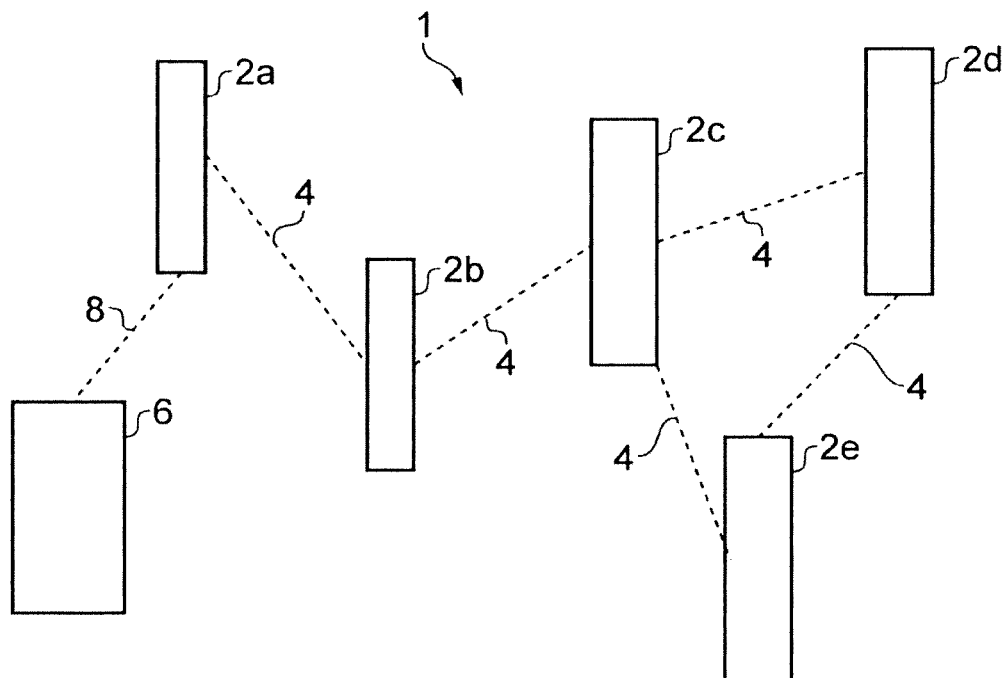
FIG. 2 schematically illustrates an example devices environment.
Figure 3:
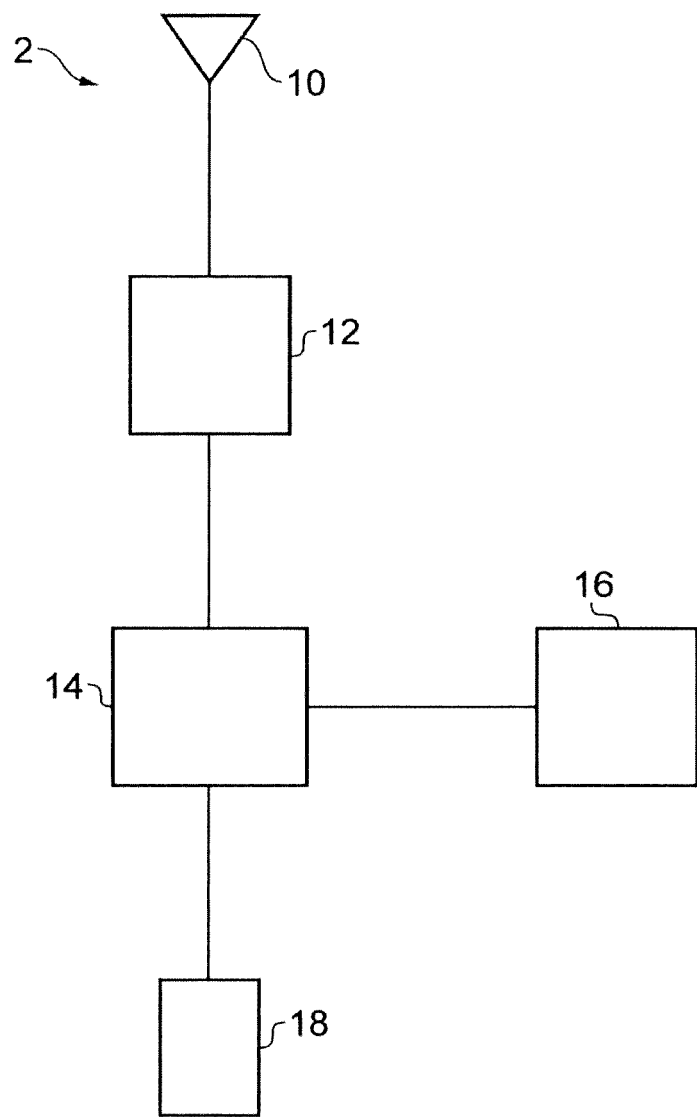
FIG. 3 schematically illustrates functional components of an aerosol provision device.
Figure 4:
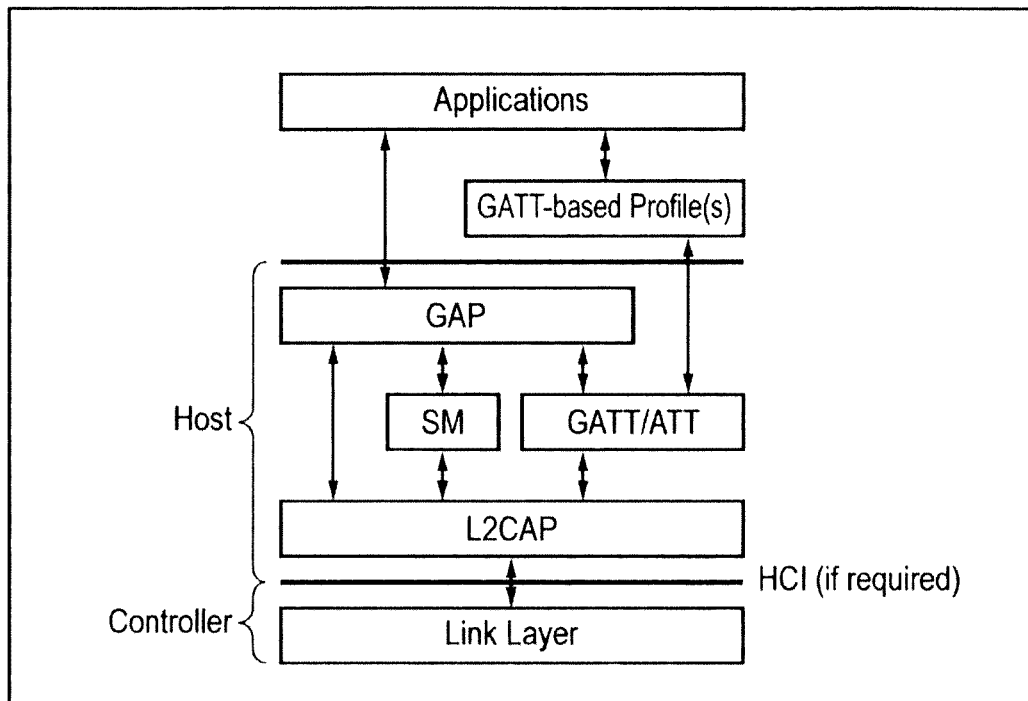
FIG. 4 schematically illustrates a protocol stack.

A first example of a devices environment 1 in which the present teachings can be utilized is shown in FIG. 2. In this example, a number of aerosol provision devices 2*a* through 2*e* are present in the devices environment 1. Various of the aerosol provision device 2 are interconnected via wireless links illustrated by dotted lines 4. However, not every aerosol provision device 2 is directly interconnected with each other aerosol provision device. Rather, the aerosol provision devices 2 are interconnected in a mesh-like pattern with a scatter net data flow. Thus, it can be seen that for a message to pass from aerosol provision device 2*a* to aerosol provision device 2*d*, that message would be passed via aerosol provision devices 2*b* and 2*c* (and optionally also 2*e*) in order to reach aerosol provision device 2*d*. From some perspectives, it may be considered appropriate to describe these interactions as a PICONET as an alternative to using the description of meshing or meshed interaction. To provide for ease of readability this description will use the term mesh throughout.

To achieve such a mesh-like communication structure, a device consistent with the present teachings can take on more than one persona and thus can belong to more than one BTLE communication relationship and furthermore, the device can act as a central or a peripheral in one BTLE communication relationship and as a peripheral in another BTLE communication relationship. To manage the simultaneous nature of these different personas, the device of the present teachings can be operated to switch between the two personas, such that at any one time the device adopts only one persona. The switching back and forth between personas happens often enough that each communication relationship is maintained without the devices with which those communication relationships are formed concluding that the device has become unavailable and closing those communication relationships.

Switching between the personas within a given device would take place on a timescale consistent with the demands a particular application for the device. There is some random element to the switching, as illustrated with respect to FIG. 1 above. The time ranges within which the random element can operate would however be set in accordance with application demands. For example, to provide for rapid data transmission through a mesh of devices the persona switching would occur at relatively high frequency. For example in an implementation based upon interactions by devices associated with users in a transient location (such as where the devices are END devices in a social situation) then each device may be configured to switch roles every few seconds. On the other hand, for greater power efficiency and where data transmission speed through the mesh is of lower concern a relatively lower persona switching frequency can be used, perhaps dropping in a suitable context to switching roles only once or twice per hour. Also, the relative duration of peripheral and central roles can be altered according to the factors applicable to the implementation environment. Thus while the peripheral persona is active the device will send data as part of the advertising packet, and while the central persona is active the device will listen for devices advertising data packets.

Additionally, a device according to the present teachings can have multiple central personas, which can be used to communicate in different meshes or to increase the total number of peripherals with which it can hold bond relationships at any one time above a limit imposed by the particular Bluetooth chipset deployed. These multiple central personas can be implemented by using the persona switching approach outlined above, or by implementing multiple BTLE MCUs.

By using such a technique, for example, the interconnections between the aerosol provision devices 2 could occur in the form of aerosol provision device 2*a* acting as central and aerosol provision device 2*b* acting as peripheral in a first BTLE relationship. Aerosol provision device 2*b* may also act a central in a second BTLE relationship that features aerosol provision device 2*c* as a peripheral. Aerosol provision device 2*c* may in turn be the central in a third BTLE relationship that includes aerosol provision devices 2*d* and 2*e* as peripherals. Further, aerosol provision device 2*d* may be also be central in a fourth BTLE relationship that includes aerosol provision device 2e as a peripheral. As will be appreciated, other orderings of which aerosol provision devices function as central and peripheral in various possible aerosol provision device relationships can be implemented. For example, the connectivity shown in FIG. 1 could alternatively be provided by having aerosol provision device 2*b* function as central in a BTLE relationship in which aerosol provision devices 2*a* and 2*c* are peripherals, and by having aerosol provision device 2*d* function as central in a relationship in which aerosol provision device 2*c* is a peripheral, and by having aerosol provision device 2*e* function as central in a relationship in which aerosol provision devices 2*c* and 2*d* are peripherals. As will be seen from the discussion below, the arrangement of relationships to make up the mesh may be determined on an ad-hoc basis depending upon which aerosol provision devices become centrals as a result of the relationship establishment process.

The mesh approach set out in the present disclosure allows the passing of small data packets or tokens between aerosol provision devices without a need to establish full BTLE bond relationships between the aerosol provision devices. Thus such tokens may be flooded through a mesh of any two or more aerosol provision devices based upon transient or impermanent aerosol provision device to aerosol provision device relationships where the peripheral to central relationship lasts just long enough to transmit and receive the token. This approach does not prevent some or all of the aerosol provision devices in the mesh establishing bond relationships (also known as pairing). Such a bond-based approach may be used for example in circumstances where volumes of data larger than can be accommodated using tokens need to be transmitted between aerosol provision devices in the mesh.

As also illustrated in FIG. 2, an additional device 6 may be provided. The device 6 need have no knowledge or capability in respect of the meshable interconnectivity of the aerosol provision devices 2 and instead implements the communication protocol in a conventional way. For example, the device 6 implements a conventional BTLE interface and is able therefore to establish a connection 6 with one of the meshable aerosol provision devices 2 such that the device 6 acts as central and the aerosol provision device 2 acts as periphery. Alternatively, the device may utilize the same meshable interconnectivity in order to communicate with one or more of the aerosol provision devices 2.

Accordingly, it will be seen that the approach of the present teachings allows a Bluetooth or BTLE-based mesh to be established without a controlling device that provides a core node for a star-type topology. The mesh can interact with a non-meshed device, but this interaction can be either continuous or intermittent and the non-meshed device need not have any role in establishing, controlling or configuring the mesh.

Therefore, by establishing such a mesh network, the various aerosol provision devices 2 can communicate with each other and pass information on to other devices within range using an existing communication protocol such as BTLE. However, as will be appreciated from the discussion, the device uses a modified form of the Bluetooth hardware implementation with Generic Attribute Profile (GATT) Notification to achieve this ad-hoc meshable behavior. As will be appreciated from the present teachings, this modification can be achieved by implementing a modified hardware, firmware or software implementation of the protocol, for example by using an implementation of a controller circuit that complies in many respects with the standard communication protocol, but includes additional functionality provided for example using a script to achieve the device-to-device interactions described herein. The additional functionality may be introduced using modified hardware which, while this involves using non-standard hardware, does provide that the hardware could provide both modes on a full time basis without the need for time-divided sharing of the personas. The controller circuit may be a hardware circuit with functionality provided by its configuration, such as an application specific integrated circuit (ASIC) or may be a programmable microprocessor (μR) or microcontroller (MCU) operating under firmware and/or software control.

FIG. 3 illustrates schematically the functional components of each aerosol provision device 2. Each aerosol provision device 2 has an antenna 10 for transmitting and receiving BTLE signals. The antenna 10 is connected to a wireless communication interface 12, for example a BTLE control circuit 12 such as a BTLE MCU. The wireless communication interface 12 receives data for transmission from and provides received data to a device core functionality processor 14 which operates, for example in conjunction with memory 16 and/or I/O elements 18 to carry out the core computing functionality of the aerosol provision device 2. Although it has been shown in FIG. 3 that the functional components of the aerosol provision device 2 interact on an direct link basis, it will be understood that as FIG. 3 is schematic in nature, this description also includes alternative arrangements of the functional components, for example on a bus interconnect basis. It will also be appreciated that one or more of the functional components illustrated may be provided by a single physical component, and also that one functional component may be provided by multiple physical components.

With regard to the functional components relating to the core computing functionality of the aerosol provision device 2, it will be appreciated that the nature and usage of these components may differ depending upon the nature of the device itself. In the example of the aerosol provision device 2, the core computing functionality may include passing or information tokens between aerosol provision device devices, monitoring and reporting of device charge and/or nicotine fluid levels, lost and found interactions, and usage recording. Thus it will also be appreciated that the core computing functionality may differ from a user-perceived core functionality of the device. For example, in the case of an aerosol provision device, the user-perceived core functionality will likely be that of aerosol generation for nicotine delivery, with the computing functionalities being additional, supplementary or secondary to that user-perceived core functionality.

FIG. 4 then illustrates schematically a protocol structure as implemented by the wireless communication interface 12 of each aerosol provision device 2. The protocol structure illustrated in FIG. 4 corresponds to the Bluetooth stack, which includes the GATT (generic attribute protocol), GAP (generic access protocol), SM (service manager protocol), GATT/ATT (low energy attribute protocol), L2CAP (logical link control and adaptation layer), and link layer. In the present examples the link layer operates on a LERF (low energy radio frequency) basis. As illustrated in FIG. 4, the protocol stack can be conceptually divided between the so-called Host and Controller layers. The controller part is made up of the lower layers that are required for physical layer packets and associated timing. The controller part of the stack may be implemented in the form of an integrated circuit such as a SoC (system-on-a-chip) package with an integrated Bluetooth radio.

The layer implementations relevant to understanding the present teachings include the link layer, the L2CAP, the GAP and the low energy attribute protocol.

The link layer controller is responsible for low level communication over a physical interface. It manages the sequence and timing of transmitted and received frames, and using link layer protocol, communicates with other devices regarding connection parameters and data flow control. It also handles frames received and transmitted while the device is in advertising or scanner modes. The link layer controller also provides gate keeping functionality to limit exposure and data exchange with other devices. If filtering is configured, the link layer controller maintains a "white list" of allowed devices and will ignore all requests for data exchange or advertising information from others. As well as providing security functionality, this can also help manage power consumption. The link layer controller uses a host controller interface (HCI) to communicate with upper layers of the stack if the layer implementations are not co-located.

The logical link control and adaptation layer protocol (L2CAP) component provides data services to upper layer protocols like security manager protocol and attribute protocol. It is responsible for protocol multiplexing and data segmentation into small enough packets for the link controller, and de-multiplexing and reassembly operation on the other end. The L2CAP's has a backend interface is for the GAP that defines the generic procedures related to the discovery of BTLE devices and link management aspects of connecting to other BTLE devices. The GAP provides an interface for the application to configure and enables different modes of operation, e.g. advertising or scanning, and also to initiate, establish, and manage connection with other devices. The GAP is therefore used control connections and advertising in Bluetooth. GAP controls device visibility and determines how two devices can (or cannot) interact with each other.

The low energy attribute protocol (ATT) is optimized for small packet sizes used in Bluetooth low energy and allows an attribute server to expose a set of attributes and their associated values to an attribute client. These attributes can be discovered, read, and written by peer devices. The GATT provides a framework for using ATT.

As will be apparent from the discussions above, the present teachings use the advertising process to facilitate the meshed interaction of multiple devices, for example to permit scattering information between an unlimited number of devices for the purpose of disseminating data over distances and time.

Figure 5:
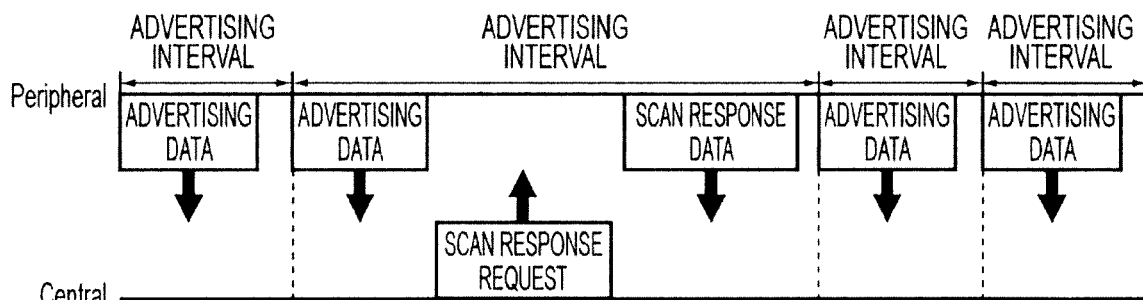
FIG. 5 schematically illustrates scan response timing.

In the context of the present examples, an application running on a device communicating via the meshed structure described herein may request or watch for specific scan response payloads, responsive to a scan response being sent by that device. This approach is used in conventional Bluetooth implementations to transmit the device name and other identification details. However in the present approaches, this scan response, which is defined as a 31 byte data packet, also referred to as a token, is used to share ID information related to a variable that when read by an application will trigger a particular response or action. The timing of such requests is illustrated in FIG. 5. As can be seen from this Figure, the scan response request is transmitted by the central device during the advertising interval and the scan response data is provided by the peripheral before the start of the next advertising interval.

By implementing the approach of the present teachings, data passing over the physical layer is indistinguishable at that level from ordinary BTLE traffic. Also, although higher-level layers are modified to accept the present meshable-interaction of devices, a non-meshable enabled application can communicate over BTLE using a device consistent with the present teachings.

Also, a device that utilizes only a conventional BTLE stack (such as device 6 illustrated in FIG. 2 above) can communicate with an aerosol provision device 2 that uses the meshable approach of the present teachings. The conventional BTLE device can then receive data from the meshable aerosol provision device 2 without the BTLE stack in the conventional BTLE device having any knowledge of the meshed interactions of the aerosol provision devices 2. The data that the conventional BTLE device receives may have originated at the directly connected aerosol provision device 2, or may have originated at aerosol provision device that previously connected to the directly connected aerosol provision device 2 via the mesh and which data has been stored or cached at the meshable aerosol provision device 2. The origin of such mesh-transferred data could be another meshed aerosol provision device 2, or could be another conventional BTLE device that is or has been connected to a meshed aerosol provision device.

Figure 6:
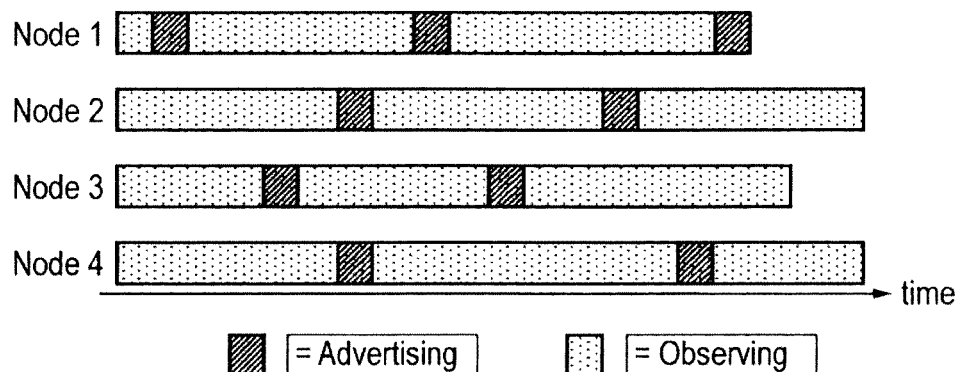
FIG. 6 schematically illustrates mode scheduling.

FIG. 6 illustrates schematically the behavior of each aerosol provision device 2 in relation to managing the dual persona nature of each aerosol provision device 2 to establish connections as both central and peripheral. As BTLE provides for two operating modes at the presentation layer, one corresponding to each of central and periphery roles, the aerosol provision device 2 of the present examples alternates between these two modes so as to provide for both advertiser broadcasting to advertise its capability as a peripheral and for observer activity to look for other peripheral-capable aerosol provision devices to which it can connect as central. While acting as observer, the aerosol provision device can act upon any received broadcaster advertisement to establish a connection as central in accordance with the usual BTLE conduct, for example as set out in the BTLE Generic Access Profile (GAP). While performing advertiser broadcasting, it will be able to establish a connection as peripheral with an observing aerosol provision device that responds to become a central. As is discussed above, this time-sharing between the personas of central and peripheral carries on after the connections between the devices have been established. This provides that the single device can operate in both modes on an ongoing, albeit time multiplexed, basis based upon a single BTLE MCU in the device.

Thus an aerosol provision device configured to provide the meshable-interaction of the present example uses the standard BTLE GATT (Generic Attribute Profile) specification in combination with a modified GAP to adopt the two operation modes associated with the dual-persona nature of the aerosol provision device. As will be discussed below, the aerosol provision device alternates between advertising as a peripheral and listening as a central so as to facilitate being able to connect to other aerosol provision devices in both central and peripheral modes. Typically the device already has an indication of the identity of the mesh in that the devices can be pre-programmed to use a particular UUID tied to the particular device mesh ("service" in BTLE terms) that the devices are intended to participate in. For example all END devices from a particular brand, range, or manufacturer may be programmed to use the same UUID. Within this context, to identify the active persona or mode, the aerosol provision device uses an ID code that uniquely identifies the aerosol provision device within the mesh. The ID and UUID (in effect mesh ID or group ID) codes are held in the firmware of the device and inserted into the advertising packets along with the data that makes up the token and may also be referenced in scan response requests and scan response messages as part of the advertising under GAP interactions with and between the devices.

While operating as a central, the aerosol provision device can adopt the states Scanner, Initiator and Master, and while operating as a peripheral the aerosol provision device can adopt the states Advertiser and Slave.

FIG. 6 also illustrates the relative advertising and observing times of multiple aerosol provision devices. The illustrated approach tends to avoid (but not necessarily exclude) multiple aerosol provision devices in range of one another performing broadcast simultaneously. In the present example, the duration of the observing period is controlled to fall in the range of 0.01 ms and 5 s, and the advertising period is of a fixed duration which may be in the range of 0.5 s to 10 s. In other examples, the advertising duration may also be variable and the observing duration may fall within a different range, overlapping range or subset of the example range given above. Such time offsetting can be achieved in a number of ways such as by coordination between the aerosol provision devices, or by each aerosol provision device using an interval length adjustment such as to provide uneven time spacing between each mode transition. Such interval length adjustments could be provided by selecting for each interval one of a number of possible interval lengths or by using some form of interval duration randomizer.

When an aerosol provision device is observing with a view to establishing a role as a central in a mesh, the aerosol provision device acts no differently to an aerosol provision device with no meshing capability when listening for advertisement from a potential peripheral aerosol provision device. Thus an aerosol provision device operating in this mode can also become a central to a conventional BTLE device without the meshing capability of the present teachings.

When an aerosol provision device is advertising with a view to establishing a role as a peripheral in a mesh, it advertises using a structure based upon the BTLE GAP data. However the BTLE GAP structure is modified to include mesh-specific information that can be recognized by a mesh-capable device which receives the advertisement. The mesh-specific information can include fields such as:

the ID of the advertising aerosol provision device;
packet sequence number of a packet awaiting transmission from that aerosol provision device, this is used to avoid duplicates—depending on the application, this may simply be a packet sequence of packets originated from that aerosol provision device (for example where the application requires only that the payload or token from the advertising aerosol provision device is flooded to multiple other aerosol provision devices) but could be made unique for a given mesh (group ID), time window and/or other uniqueness scope according to the application requirements;
source aerosol provision device identifier of the packet having that packet sequence number, to reflect that the token now being passed may have originated at a different aerosol provision device to the one that is now passing it on;
destination aerosol provision device identifier for the packet having that packet sequence number, depending on the implementation this can be an single aerosol provision device (corresponding to some form of routed operation) or 'all' aerosol provision devices (corresponding to flooding type operation);
the group ID of the source aerosol provision device for the packet having that sequence number, which is used to allow multiple mesh networks to co-exist in the same physical space (as explained above, this group ID typically uses the BTLE UUID, although another group ID filed could be defined and used if required);
life time or expiry time of the packet having that sequence number;
payload, the data specific to a particular application—for example data relating to an END device application.

In accordance with the BTLE data handling approach, if a given application payload item is too large for a single packet, that payload item is broken down and distributed within multiple packets before reassembly at the/each destination aerosol provision device. In such applications a bond may be established between aerosol provision devices so as to provide for more transmission management for this larger data volume.

Figure 7:
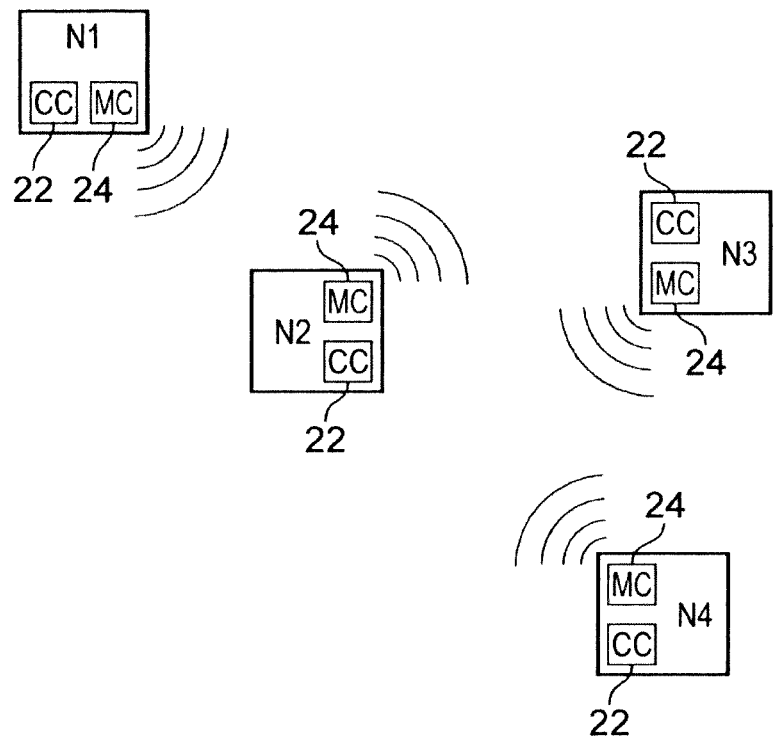
FIG. 7 schematically illustrates a mesh of nodes.
Figure 8:
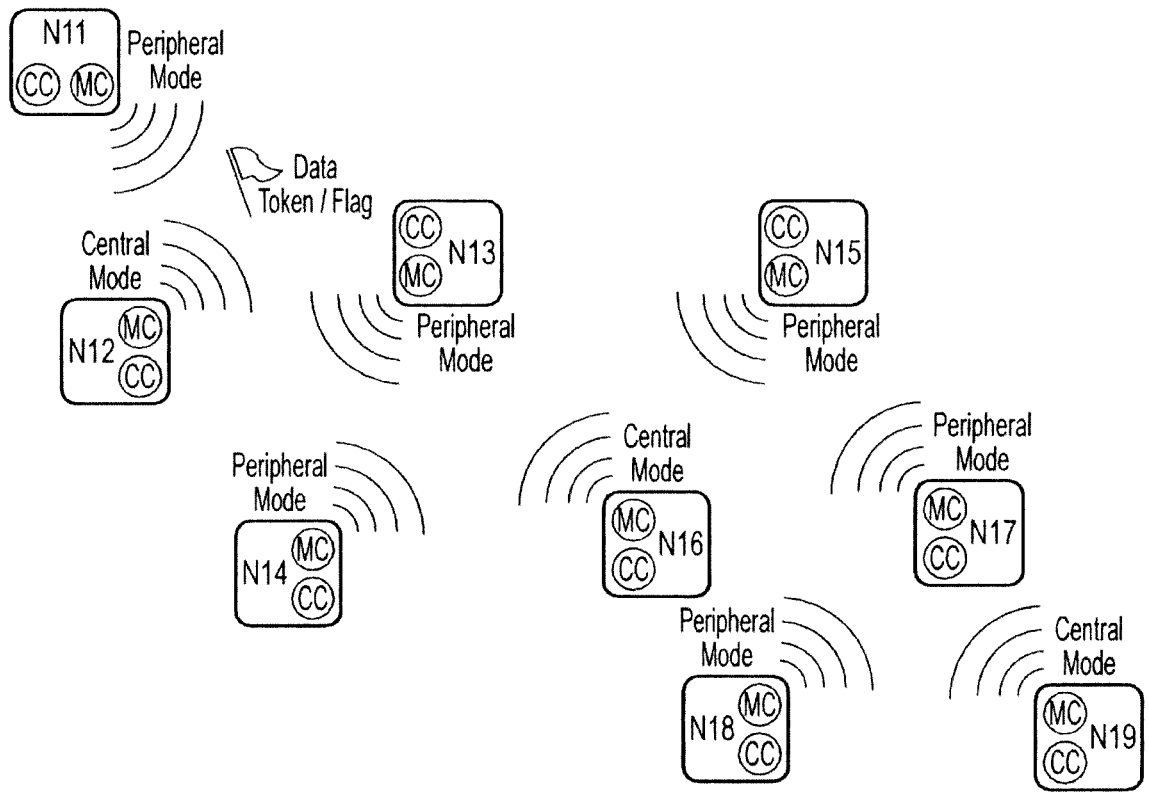
FIG. 8 schematically illustrates a mesh of nodes.

FIG. 7 schematically illustrates connectivity patterns between a number of aerosol provision devices N1, N2, N3 and N4. In this illustration, aerosol provision device N1 is out of range for direct communication with aerosol provision device N4. Different operation modes of the aerosol provision devices are signified by the elements control chip (CC) 22 and mesh chip (MC) 24 of each of aerosol provision devices N1 to N4. The control chip is representative of the aerosol provision device MCU operating to communicate with a conventional BTLE device such as the device 6 shown in FIG. 2. The mesh chip is representative of the aerosol provision device MCU operating in both central and peripheral modes to communicate through the mesh.

In the example of FIG. 7, aerosol provision device N1 has a bit set in an advertisement data field indicating that it has data to send. The schedule of advertising and observing in each aerosol provision device causes aerosol provision device N2 to be the first aerosol provision device in direct communication range with N1 to listen as a central following aerosol provision device N1 having the advertisement data field set. Thus aerosol provision device N2 when in central mode receives the advertising data which N1 is advertising while in peripheral mode. This advertising data, as received by N2 can be used by N2 in connection with an application running at or otherwise associated with N2. In addition or alternatively, aerosol provision device N2 can cache the advertising data ready for onward transmission as advertising data on a future occasion that aerosol provision device N2 adopts its peripheral persona. Thereby, the advertising data that originated at N1 can pass onward from N2 as advertising data that it then received by aerosol provision device N3 at a time when N2 is advertising as peripheral and N3 is listening as central. The advertising data that originated with N1 can then be used and/or passed on by N3, ultimately arriving at N4 by the same method.

It should be noted that in this implementation, the advertising data is effectively flooded across the mesh. Thus, if N1 happens to be listening as central at the same time that N2 is advertising as peripheral, the advertising data will return to N1 as well as passing onward through the mesh to N3. In this circumstance either the aerosol provision device N1 or some application running at or associated with N1 may simply discard the returning advertising data. In some implementations, the aerosol provision device or application may make use of the returned advertising data in some way, for example using the time between transmission and receipt as some form of random interval generator or for mesh diagnostics.

As has been explained above, it is possible for the transmission over the mesh to be in the more structured format of using established bonds between the aerosol provision devices. In such a circumstance, each pair of aerosol provision devices will interact over an established bond and the persona switching at each aerosol provision device will provide for data received in a bond of which one persona is a member can then be onwardly transmitted using a bond of which the other persona is a member.

Control as to whether the data is transmitted to every aerosol provision device (flooding) or whether the data is transmitted only to selected aerosol provision devices (routing) can be achieved in several ways. If the data is to be automatically communicated to all aerosol provision devices without restriction, then this can be a default state configured into the aerosol provision devices. If the data is to be transmitted only to aerosol provision devices currently active in the mesh, then this can be achieved either as default behavior set in the aerosol provision devices or on an application-specific basis where the application is mesh-aware and provides control information to the communication stack to indicate the data transmission extent. If the data is only to be transmitted to specific aerosol provision devices, this can be achieved on an application-specific basis where the application is mesh-aware and provides control information to the communication stack to indicate the data transmission extent. The present examples are configured to operate on the basis of a flooding approach such that data is automatically forwarded to all presently-meshed devices.

FIG. 8 provides a further illustration of meshing behavior as between aerosol provision devices. In this example, a larger number of aerosol provision devices N11 to N19 are present. The illustration in FIG. 8 represents a given snapshot in time such that different ones of the aerosol provision devices are illustrated as having currently adopted different ones of their respective peripheral and central personas. At the time illustrated in FIG. 8 three aerosol provision devices have become configured into central mode, these being aerosol provision devices N12, N16 and N19, with the remaining aerosol provision devices having become configured into peripheral mode. As will be appreciated from the discussion above, for any given instance of the same aerosol provision devices being present in the same locations, the exact number and identify of the aerosol provision devices that become configured into the central mode will depend upon factors such as the scheduling by each aerosol provision device of its advertising/observing periods and the relative location of each aerosol provision device compared to any other aerosol provision device that has already become configured into either central or peripheral mode. The passing of a data token is illustrated in the figure by the presence of a flag passing from N11 sending this data token in its advertising data to N12 which will receive that advertising data listening in central mode. This token will later be included in advertising data from N12 when N12 adopts its peripheral persona. Thereby the token can be passed onward through the mesh and ultimately arrive at each aerosol provision device in the mesh at least once.

As will be understood from the discussion above, the meshes can change dynamically based upon changes to the numbers and positions of aerosol provision devices in the mesh. For example as aerosol provision devices move away from the remainder of the mesh, eventually they will lose contact with all aerosol provision devices in the mesh and leave the mesh. Likewise, an aerosol provision device that is deactivated or enters a power saving non-wireless mode will lose contact with the other aerosol provision devices in the mesh and leave the mesh. Further, new aerosol provision devices not previously a part of the mesh will be able to join the mesh as and when they come within range of an aerosol provision device in the mesh or when they are powered while within range of an aerosol provision device in the mesh. Also, as will be understood from the discussion of persona switching above, an aerosol provision device already within the mesh and operating as a peripheral within the mesh will also operate at a different time as a central within the mesh. In an implementation in which the mesh adopts bond relationships such that particular aerosol provision devices have defined roles as centrals in some bonds and peripherals in others, if an aerosol provision device then changes location relative to the aerosol provision devices in the mesh it may in effect leave the mesh as all established bonds may cease to operate of the range to the new location. Such an aerosol provision device would then resume attempting both observing and advertising until it establishes one or more new bond relationships into other aerosol provision devices of the bond-linked mesh.

As the skilled reader will appreciate, Bluetooth and BTLE provide for securing of an inter-node communication bond. This is not applicable to the purely advertising-based transmission of tokens in the form of advertising data unless such transmission of tokens leads to the establishment of bond relationships. In the present examples, even where bond relationships are used, the aerosol provision devices can be configured to establish such bonds without requiring user input to confirm trust between the different aerosol provision devices or other devices. Rather, in the present examples, aerosol provision devices of a particular type can be configured to pre-trust all other aerosol provision devices of that particular type. For example, each aerosol provision device can be configured to trust all other devices that identify as being aerosol provision devices from a given manufacturer, group of manufacturers, brand, group of brands, model, group of models or as being compliant with a given aerosol provision device standard or group of standards.

Such a trust pattern can be supplemented with inherent controls on the amount of personal data that the device stores/is permitted to transmit. For example, an aerosol provision device may be configured by the owning user to not hold or to be prevented from sharing any information that identifies the owner. This would not preclude the END device from interacting with other END devices to pass on information that can be used for lost/found functionality or from passing on information about the END device itself to provide for group interactions between END devices of the same brand or model, for example as discussed below.

In other examples, trust may be a user-explicit functionality, such that a user may be required to actively accept or request a communication bond to be established with another aerosol provision device.

Where a particular aerosol provision device or other device is being configured by the user, for example to communicate with a conventional BTLE device of the user such as a smartphone, phablet or tablet device, the trust relationship between the user's meshable device and conventional BTLE device may be secured in the same manner as other conventional BTLE pairings to establish a communication bond.

Thus it will be understood that by using the approach of the present teachings, a device can be provided that is capable of meshed interaction with other similar devices by adopting a dual-persona structure in which the device is able to operate on a time-division basis as both a master (central) and slave (peripheral) for communication with those other like devices while also operating as a slave/peripheral to a conventional device without the dual persona capability.

This approach can be used to facilitate device-to-device interactions between a range of devices for a range of purposes. As discussed above, examples of devices that can be equipped for such device-to-device interactions using the meshed or PICONET topology approach of the above examples include electronic nicotine delivery devices (END devices).

The meshable interconnectivity of the aerosol provision devices 2A and one or more other devices as described above may be considered a connectionless-state interaction, wherein connectionless-state packets are created, transmitted and received by each device in accordance with the examples described above with reference to FIGS. 1 to 8.

In the present example, the wireless communication interface 12 of an aerosol provision device 2a is used to create a connectionless-state advertising packet that contains information relating to at least one physical characteristic of the aerosol provision device 2a. The at least one physical characteristic may include the color of the aerosol provision device 2a. The at least one physical characteristic may also include other physical characteristics such as the shape of the aerosol provision device 2a, the size of the aerosol provision device 2a and the type of the aerosol provision device 2a. For example, the at least one physical characteristic of the aerosol provision device 2a may include the length, width and thickness of the aerosol provision device 2a, and/or an indication that the aerosol provision device 2a is substantially cylindrical in shape, pebble shaped, oval shaped or another geometric shape.

The color of the aerosol provision device 2a may be conveyed as a hex color code, which could be either a hex code approximating to the actual color of the device or a code illustrating very generally the color property. For example, if the aerosol provision device 2a was a red device, as a general approximation of "red" this could be represented by the hex color code FF0000, while a specific hex code for the actual color could correspond to a pantone or other color identifier of the device (as one example a device colored in Pantone 2347 U, would be represented by the hex code E74536 or for simplicity of representation of the color on a display device could be approximated to the so-called websafe color FF3333). In the example of a yellow device, the general approximation of "yellow" could be represented by the hex color code FFFF00, while a specific hex code for an actual color might correspond for example to Pantone 114 C would be represented by the hex code FBDD40 (or for simply display of the color on a display device could be approximated to the so-called websafe color FFCC33). Conveying the color of the aerosol provision device 2a as a hex color code allows any of the colors in the RGB color model to be conveyed in the advertising packet using 3 bytes. Alternatively, the color of the aerosol provision device 2a could be conveyed using a predetermined code. For example, if a particular type of aerosol provision device 2a were only manufactured in a finite number of different colors, such as eight, a code would be used to convey the color of the device, such as 001 for red, 010 for yellow, 011 for blue, etc., through the available color extent. In this way, only three bits in a single byte of the advertising packet is required to convey the color of the aerosol provision device 2a, thereby saving space in the advertising packet.

In the present example, the advertising packet generated by the wireless communication interface 12 of an aerosol provision device 2a optionally includes additional information about the aerosol provision device 2a, such as the batch number (batch ID) of the aerosol provision device 2a, the serial number of the aerosol provision device 2a and/or the product identification number (product ID) of the aerosol provision device 2a. For example, the advertising packet may include a UUID corresponding to the aerosol provision device 2a.

Figure 9:
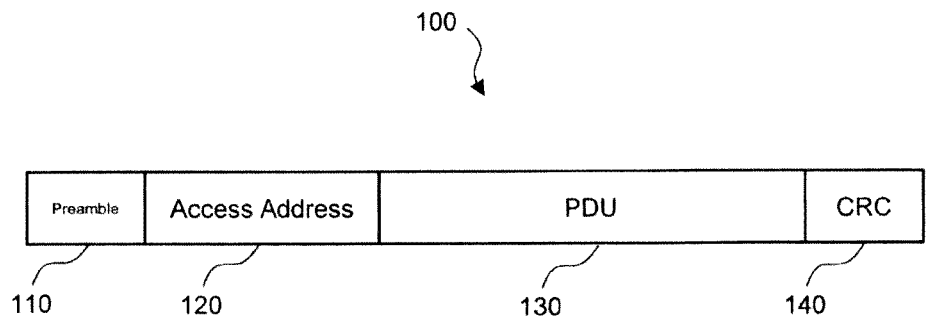
FIG. 9 schematically illustrates an example BLE advertising packet.

The wireless communication interface 12 of an aerosol provision device 2a may be a Bluetooth low energy (BLE) communication interface. FIG. 9 illustrates schematically an example BLE advertising packet 100, which is up to 47 bytes in size. Such an advertising packet is generated by the BLE communication interface 12 of the aerosol provision device 2a.

The advertising packet 100 illustrated in FIG. 9 begins with a 1 byte preamble 110 and a 4 byte access address 120, the access address 120 corresponding with the RF channel number used by to transmit the advertising packet 100. The preamble 110 and access address 120 portions are followed by the Packet Data Unit (PDU) 130, which can between 2 and 39 bytes in size depending on the advertising type used. The advertising packet 100 then finishes with a 3 byte Cyclic Redundancy Check (CRC) 140. The content and format of the preamble 110, access address 120 and CRC 130 portions may be standardized across each advertising packet 100, but the length and content of the PDU 130 may be different for each advertising packet 100. The length of the PDU 130 is typically kept to the minimum required to convey the required information in order to reduce the transmission time of the advertising packet 100.

Figure 10:
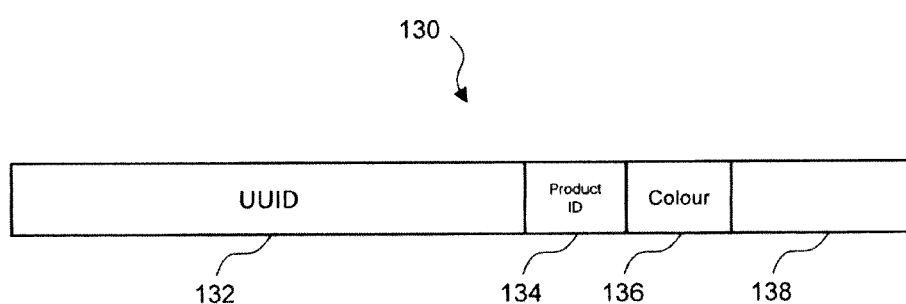
FIG. 10 schematically illustrates a PDU of an example BLE advertising packet.

FIG. 10 illustrates schematically the PDU 130 of an example BLE advertising packet 100, for example the BLE advertising packet 100 illustrated in FIG. 9. In this example, the first 16 bytes of the PDU 130 contain a 128 bit UUID 132 of the aerosol provision device 2a. The next 2 bytes of the PDU 130 contain the product ID 134 of the aerosol provision device 2a. The next 3 bytes contain the hex color code 136 corresponding to the color of the aerosol provision device 2a. The remaining bytes 138 are unallocated, but may be used to convey additional information, such as the shape of the aerosol provision device 2a, the size of the aerosol provision device 2a and/or the type of the aerosol provision device 2a. The batch ID of the aerosol provision device 2a may be included instead of the product ID 134, or the batch ID may be included in the unallocated portion 138 of the PDU 130. Alternatively, the allocation of space for the color information may be a single byte for example where the color of the aerosol provision device 2a is conveyed using a predetermined code.

The wireless communication interface 12 of the aerosol provision device 2a is then used to transmit the generated advertising packet via a wireless communication network. For example, if the wireless communication interface 12 is a BLE communication interface, the advertising packet 100 may be in the format illustrated in FIGS. 9 and 10. The advertising packet 100 is then received by a device 6 listening for an advertising packet in a mesh network as described above.

Figure 11:
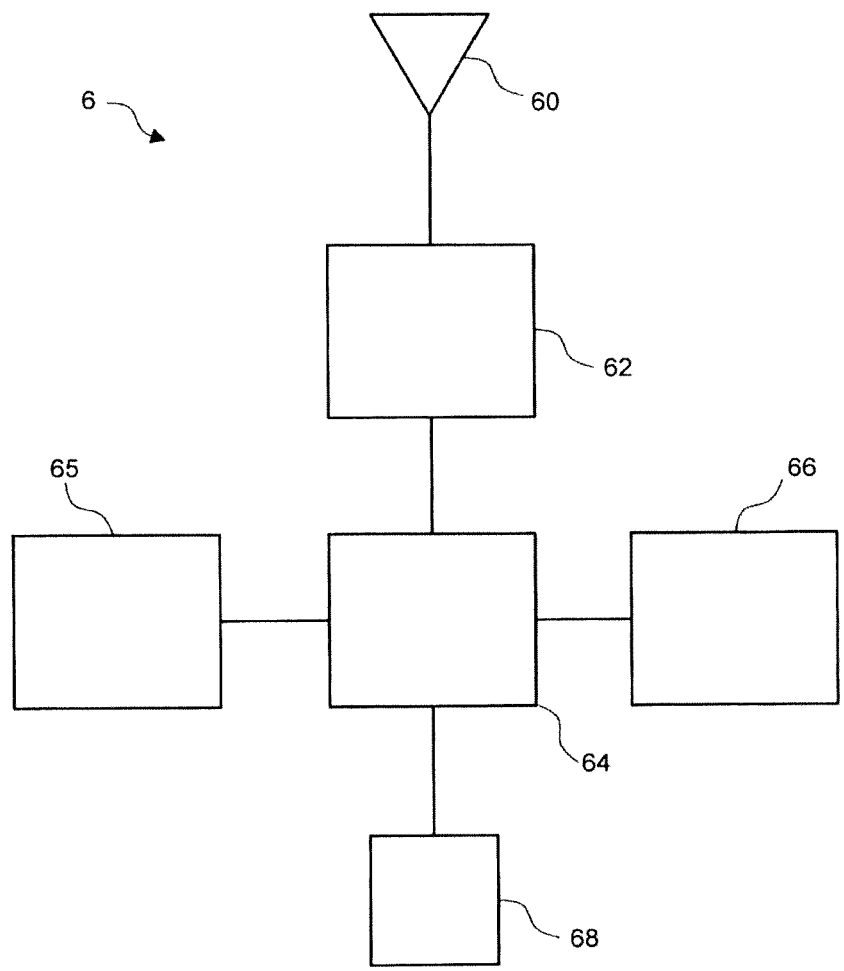
FIG. 11 schematically illustrates functional components of a portable electronic device.

FIG. 11 illustrates schematically the functional components of a portable electronic device 6. The portable electronic device 6 may be a mobile communications device, such as a mobile phone or smartphone or a portable computing device such as a laptop, smartwatch, tablet or phablet device. Each portable electronic device 6 has an antenna 60 for transmitting and receiving wireless communication signals, such as BLE signals. The antenna 60 is connected to a wireless communication interface 62 capable of supporting paired interaction, for example a BLE control circuit 62 such as a BLE MCU. Within the context of BLE, a paired interaction is understood to mean both pairing and bonding. The wireless communication interface 62 receives data for transmission from and provides received data to a device core functionality processor 64 which operates, for example in conjunction with memory 66, I/O elements 68 and/or the display 65 to carry out the core computing functionality of the portable electronic device 6. The display 65 is configured to display a user interface, such as a graphical user interface (GUI), to the user of the portable electronic device 6. The display 65 may be a touchscreen display, allowing the user to interact with user interface displayed on the display 65 by touching the display 65 with their finger, stylus or other suitable object. Alternatively, the display 65 may be a conventional display screen, with the user interface including one or more buttons, switches or other input elements 68 located on, attached to or in communication with the portable electronic device 6 for user interaction. For example, the user may be able to interact with the user interface using a button located on the portable electronic device, a wired pointing device such as a mouse or a wireless device such as a wireless keyboard, wireless remote control or a smartwatch, or by speech or gesture recognition. Although it has been shown in FIG. 6 that the functional components of the portable electronic device 6 interact on an direct link basis, it will be understood that as FIG. 6 is schematic in nature, this description also includes alternative arrangements of the functional components, for example on a bus interconnect basis. It will also be appreciated that one or more of the functional components illustrated may be provided by a single physical component, and also that one functional component may be provided by multiple physical components.

Figure 12:
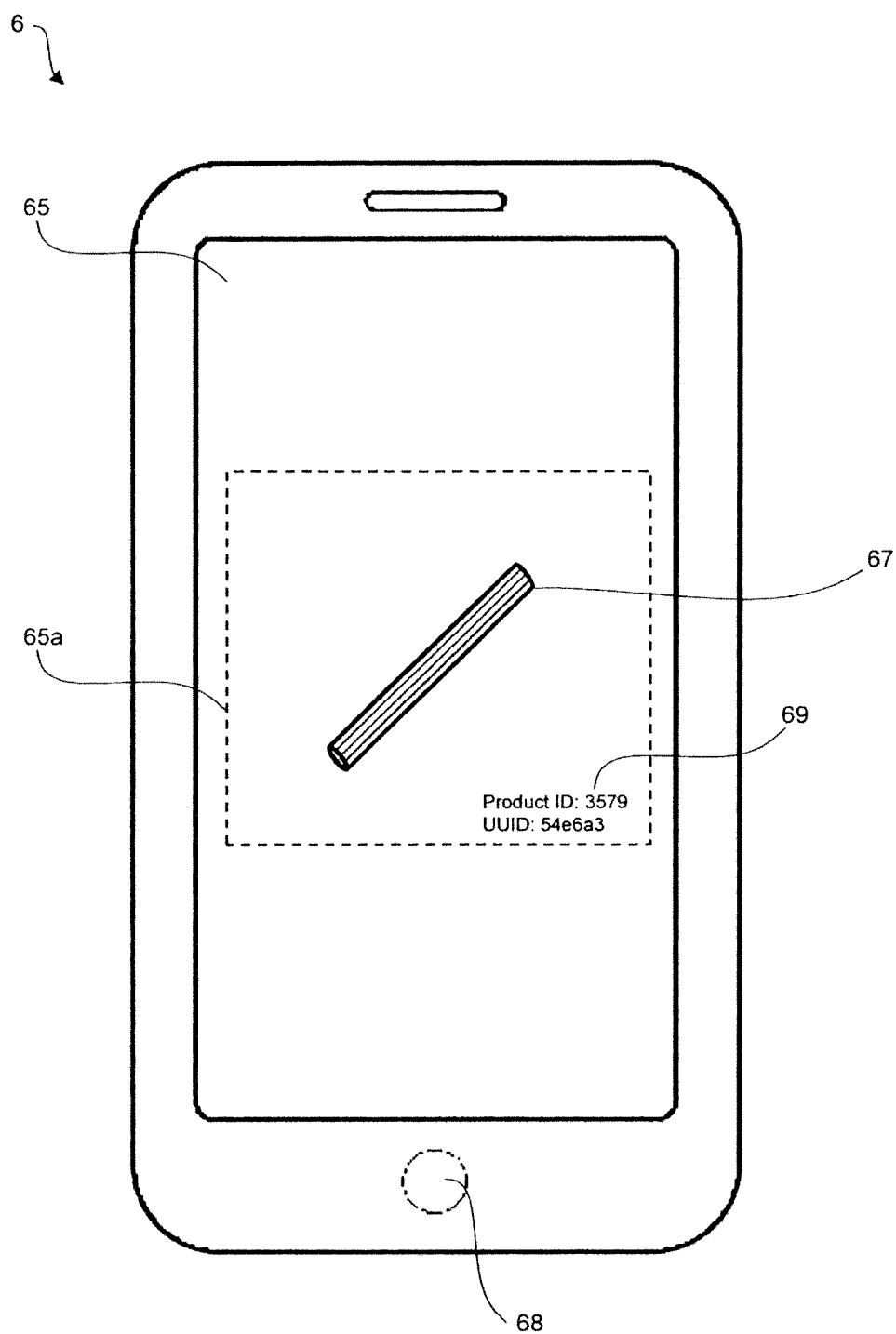
FIG. 12 schematically illustrates a user interface on a display of a portable electronic device.
Figure 13:
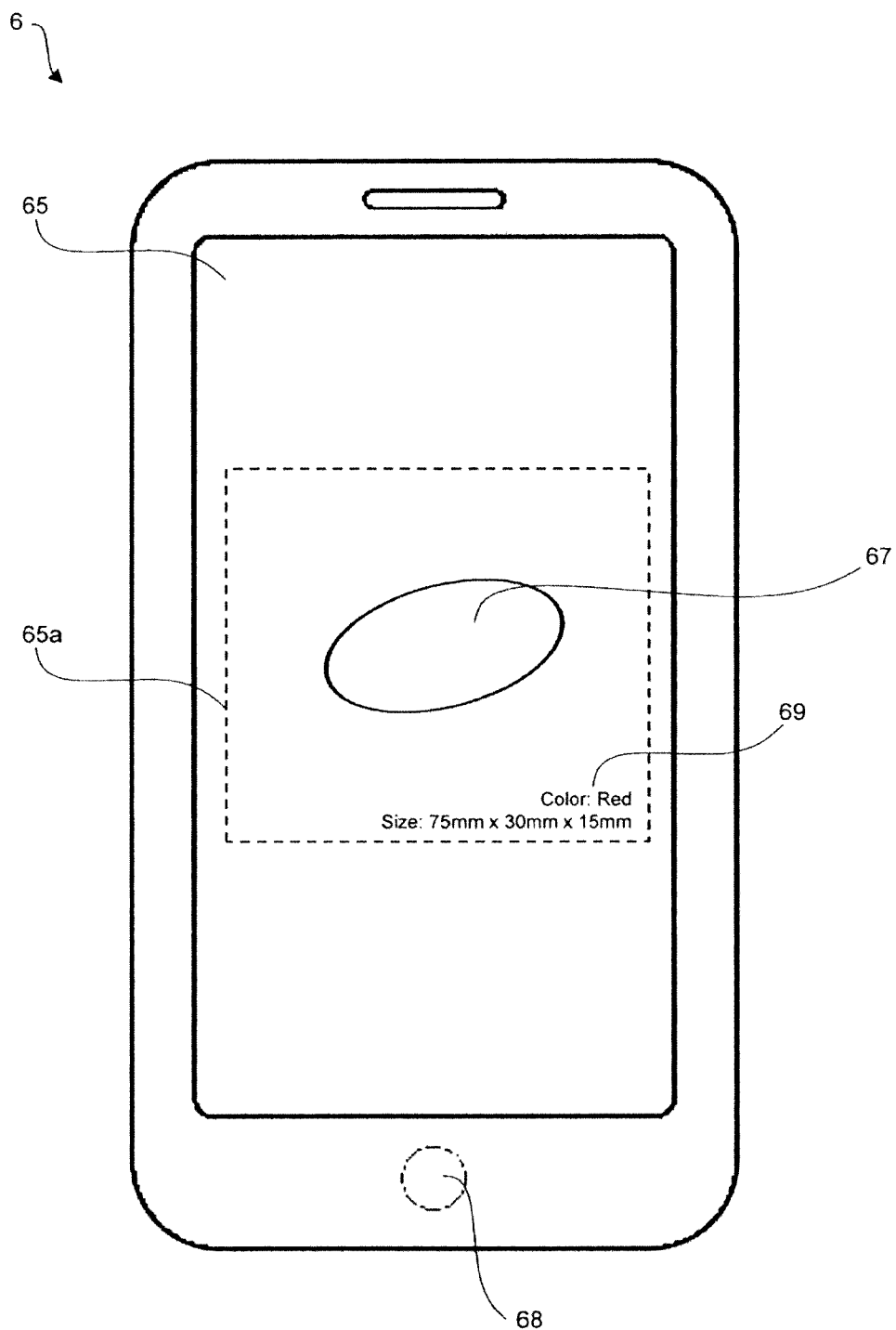
FIG. 13 schematically illustrates a user interface on a display of a portable electronic device.

In the present example, the portable electronic device 6 receives a data packet via the wireless communication interface 62 from an aerosol provision device 2a via a wireless communication network. The data packet may contain information relating to at least one physical characteristic of the aerosol provision device 2*a*, for example an advertising packet 100 as described above in relation to FIGS. 9 and 10.

In response to receiving a data packet from an aerosol provision device 2*a*, the processor 64 of the portable electronic device 6 is configured to determine the identity of the aerosol provision device 2*a* based at least in part on the at least one physical characteristic of the aerosol provision device 2*a*. For example, the processor 64 of the portable electronic device 6 may read the data packet to extract the color of the aerosol provision device 2*a*. In the example where the data packet is an advertising packet 100 as described above in relation to FIGS. 9 and 10, the processor 64 is configured to read the PDU 130 of the advertising packet 100 in order to extract the information relating to the at least one physical characteristic of the aerosol provision device 2*a*, such as the color conveyed in as a hex color code 136, the UUID 132 and the product ID 134 of the aerosol provision device 2*a*.

The memory 66 of the portable electronic device 6 may contain a database of physical characteristics of known aerosol provision devices. As part of the determination of the identity of the aerosol provision device 2*a*, the processor 64 of the portable electronic device 6 may compare the information relating to at least one physical characteristic of the electronic nicotine delivery device 2*a*, and contained in the received data packet, to information contained in the database stored in the memory 66 of the portable electronic device 6. For example, if the at least one physical characteristic in the data packet includes the shape and/or size of the aerosol provision device 2*a*, this information may be cross-referenced against information in the database in order to determine the type of aerosol provision device the data packet was sent from. Alternatively, or in addition, if the color of the aerosol provision device 2*a* is conveyed in the data packet using a predetermined code, the processor 64 may use the information in the database to translate the code sent in the data packet into a color of the aerosol provision device 2*a*.

In the present example, the processor 64 of the portable electronic device 6 is configured to change an aspect of a user interface based on the determined identity of the aerosol provision device 2*a*. This allows the user to easily identify the aerosol provision device when communicating with it for the first time using the portable electronic device. For example, the processor 64 may be configured to present a pictorial or graphical representation which indicates the aerosol provision device 2*a* on the user interface, where the graphical representation is based on the determined identity of the aerosol provision device 2*a*. FIGS. 12 and 13 schematically illustrates a user interface on a display 65 of a portable electronic device 6 corresponding to a change in an aspect of the user interface performed by the processor 64 of the portable electronic device 6. In the examples illustrated in FIGS. 12 and 13, a graphical representation 67 which indicates the aerosol provision device 2*a* is provided on a portion 65*a* of the display 65.

Alternatively or in addition, the processor 64 may change another aspect of the user interface, such as playing an animation or video, playing a sound, changing the display settings of the user interface, such as the brightness, contrast or resolution of the user interface, or changing one or more colors displayed on the user interface. Changing an aspect of the user interface based on the determined identity of the aerosol provision device informs the user as to the identity of the aerosol provision device 2*a* from which data has been received. This allows the user to determine what action to take, for example to request commencement of a pairing process between the portable electronic device 6 and the aerosol provision device 2*a*, or to block the aerosol provision device 2*a* from further communication with the portable electronic device 6.

The identity of the aerosol provision device 2*a* may be determined based on the color of the aerosol provision device 2*a* and the processor 64 is configured to change the color of at least a portion of user interface to match the color of the aerosol provision device 2*a*. For example, if the color of the aerosol provision device 2*a* is conveyed as a hex color code, the processor 64 is configured to change the color of at least a portion of user interface to the RGB color corresponding to the hex color code. Alternatively, the processor 64 may be configured to present the physical characteristic used to identify the aerosol provision device 2*a* on the user interface, such as in text form. In the example illustrated in FIG. 12, the graphical representation 67 is shaded to represent the color of the aerosol provision device 2*a*, whilst in the example illustrated in FIG. 13 the graphical representation 67 is not colored to match the color of the aerosol provision device 2*a*.

The identity of the aerosol provision device 2*a* may also be determined based on one or more of the UUID, the product ID and the batch ID of the aerosol provision device 2*a*, and the processor 64 is configured to display this information on the user interface, for example as text or in one or more images. If the identity of the aerosol provision device 2*a* is also determined based on the color of the aerosol provision device 2a, the processor 64 may be configured to change the color of at least a portion of user interface to match the color of the aerosol provision device 2a and to display the additional information, such as the UUID, the product ID and/or the batch ID, in text form in or near the portion of the user interface where the color has been changed. In the example illustrated in FIG. 12, the portion 65a of the display 65 also contains text 69 next to the graphical representation 67, the text 69 containing the product ID and the UUID of the aerosol provision device 2a. In the example illustrated in FIG. 13, instead of the graphical representation 67 being shaped to represent the color of the aerosol provision device 2a, the portion 65a of the display 65 also contains text 69 next to the graphical representation 67, the text 69 containing the color of the aerosol provision device 2a and the size of the aerosol provision device 2a The identity of the aerosol provision device 2a may also be determined based on one or more of the shape, the size and the type of aerosol provision device 2a. In such an example, in addition or alternatively to displaying this information in text form on the user interface, the processor 64 may be configured to display a pictorial representation of the aerosol provision device 2a, where the shape and size of the pictorial representation are based on the shape, the size and the type of aerosol provision device 2a used to determine the identity of the aerosol provision device. For example, if the data packet received from the aerosol provision device 2a indicates that the aerosol provision device 2a is substantially cylindrical in shape, the processor 64 is configured to display a cylinder on a portion of the user interface, for example as a plan view in 2D or an orthographic or isometric projection. In the example illustrated in FIG. 12, the graphical representation 67 is cylindrically shaped to match the shape of the aerosol provision device 2a. If the data packet received from the aerosol provision device 2a indicates the size of the aerosol provision device 2a, the processor 64 is configured to display a graphical representation which indicates the aerosol provision device 2a where the dimensions of the graphical representation are scaled relative to the size of the aerosol provision device 2a received in the data packet. In the example illustrated in FIG. 13 the graphical representation 67 is pebble or oval shaped to match the shape of the aerosol provision device 2a and the graphical representation 67 is also scaled to match the size of the aerosol provision device 2a The memory 66 of the portable electronic device 6 optionally contains a database of physical characteristics of known aerosol provision devices. Each entry in the database may include a picture or graphical representation which indicates the corresponding aerosol provision device. Accordingly, when the identity of the aerosol provision device from which the data packet was received is determined based on a comparison with entries in the database stored in the memory 66 of the portable electronic device 6, the processor 64 may be configured to change an aspect of the user interface by displaying the picture or graphical representation which indicates the entry in the database corresponding to the identity of the aerosol provision device 2a in a portion of the user interface.

Any combination of the change of an aspect of the user interface described above may be combined. For example, the processor 64 may be configured to display a graphical representation which indicates the aerosol provision device 2a on at least a portion of the user interface, where the shape and size of the graphical representation is based on shape and size information in the received data packet, the color of the graphical representation is based on the color information in the received data packet and any additional information in the received data packet, such as the UUID, product ID and batch ID of the aerosol provision device is displayed in text form next to the graphical representation or as part of the graphical representation, for example as text on the body of the aerosol provision device in the graphical representation.

The portable electronic device 6 optionally receives a data packet via the wireless communication interface 62 from a second aerosol provision device 2b via a wireless communication network. The data packet may contain information relating to at least one physical characteristic of the second aerosol provision device 2b, for example an advertising packet 100 as described above in relation to FIGS. 9 and 10. The at least one physical characteristic of the second aerosol provision device 2b contained in the data packet may be the same set of characteristics as in the data packet received from the first aerosol provision device 2a, a different set of characteristics or an overlapping set of characteristics. For example the data packet received from the first aerosol provision device 2a may contain information relating to the color of the first aerosol provision device 2a, the UUID and the product ID of the first aerosol provision device 2a whilst the data packet received from the second aerosol provision device 2b may contain information relating to the color of the second aerosol provision device 2b, the size of the second aerosol provision device 2b and the shape of the second aerosol provision device 2b.

In response to receiving a data packet from the second aerosol provision device 2b, the processor 64 of the portable electronic device 6 is configured to determine the identity of the second aerosol provision device 2b based at least in part on the at least one physical characteristic of the aerosol provision device 2b, as described above with respect to the identity of the first aerosol provision device 2a.

The processor 64 is then configured to change an aspect of the user interface based on the determined identity of the first aerosol provision device 2a and the second aerosol provision device 2b such as to enable a selection from a user of one of the first aerosol provision device 2a or the second aerosol provision device 2b. For example, the processor 64 may be configured to display information relating to the identity of the first aerosol provision device 2a on a first portion of the user interface and to display information relating to the identity of the second aerosol provision device 2b on a second portion of the user interface. The user is then able to select either the first aerosol provision device 2a or the second aerosol provision device 2b, for example by touching the portion of a touchscreen display corresponding to either the first portion of the user interface or the second portion of the user interface, by using a pointing device to position the pointer in the first portion of the user interface or the second portion of the user interface and making a selection, by pressing a button or other input element, by uttering an expression or making a gesture.

Figure 14:
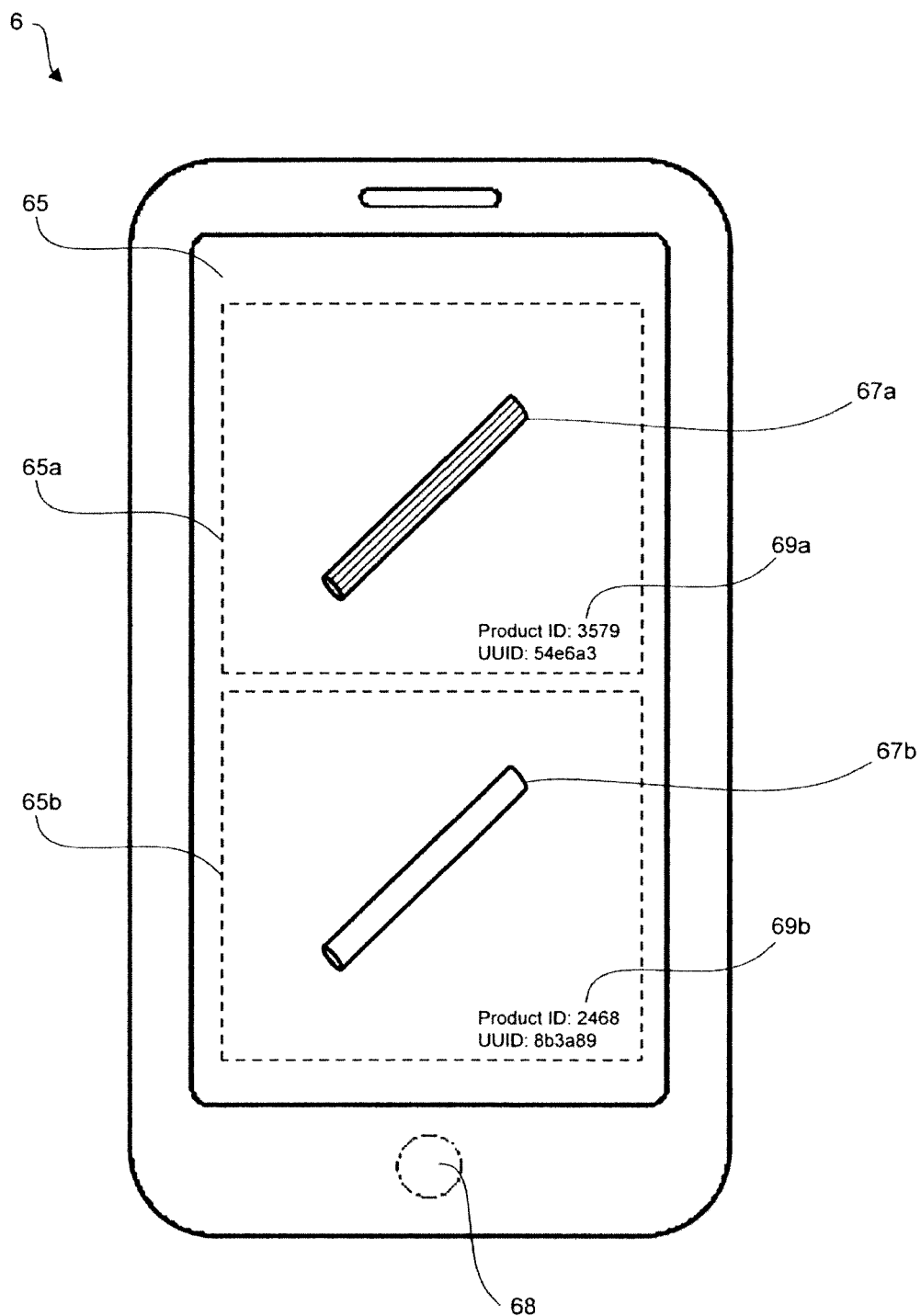
FIG. 14 schematically illustrates a user interface on a display of a portable electronic device.

FIG. 14 schematically illustrates a user interface on a display 65 of a portable electronic device 6 corresponding to a change in an aspect of the user interface performed by the processor 64 of the portable electronic device 6. In the illustrated example, a first graphical representation 67a which indicates the first aerosol provision device 2a is provided on a first portion 65a of the display 65 and a second graphical representation 67b which indicates the second aerosol provision device 2b is provided on a second portion 65b of the display 65. The first graphical representation 67a is cylindrically shaped to match the shape of the first aerosol provision device 2a, and the second graphical representation 67*b* is cylindrically shaped to match the shape of the second aerosol provision device 2*b*. The first graphical representation 67*a* is shaded to represent the color of the first aerosol provision device 2*a*, whilst the second graphical representation 67*b* is not shaded to represent that the second aerosol provision device 2*b* is white. The first portion 65*a* of the display 65 also contains first text 69*a* next to the first graphical representation 67*a*, the first text 69*a* containing the product ID and the UUID of the first aerosol provision device 2*a*. The second portion 65*b* of the display 65 also contains second text 69*b* next to the second graphical representation 67*b*, the second text 69*b* containing the product ID and the UUID of the second aerosol provision device 2*b*. The user is then able to select the first aerosol provision device 2*a* or the second aerosol provision 2*b*, for example by touching either the first portion 65*a* of the display 65 or the second portion 65*b* of the display 65 with a finger, stylus or other suitable device, by pressing the button 68 or through another selection means as described above.

Figure 15:
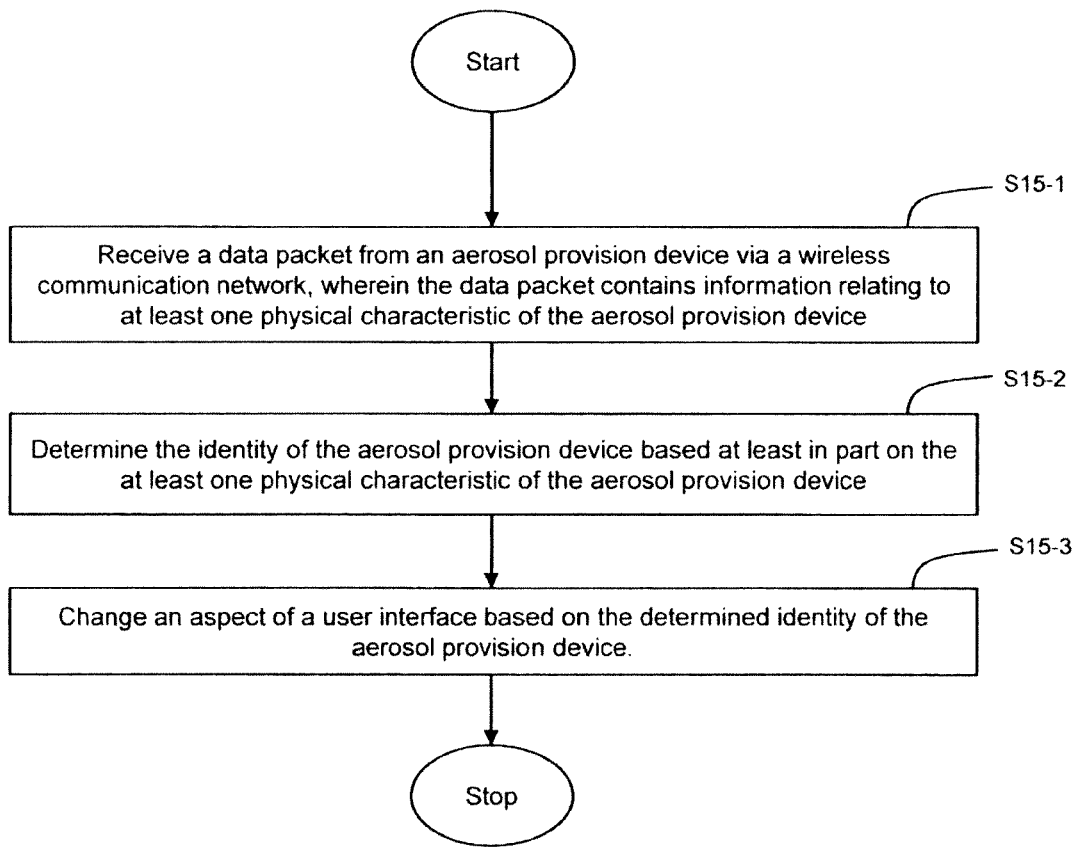
FIG. 15 illustrates a method for a portable electronic device.

FIG. 15 illustrates a method for a portable electronic device 6. At step 15-1, a data packet is received from an aerosol provision device via a wireless communication network, wherein the data packet contains information relating to at least one physical characteristic of the aerosol provision device. At 15-2, the identity of the aerosol provision device is determined based at least in part on the at least one physical characteristic of the aerosol provision device. At 15-3, an aspect of a user interface is changed based on the determined identity of the aerosol provision device.

FIG. 16 illustrates a further method for a portable electronic device 6. At 16-1, a data packet is received from a first aerosol provision device via a wireless communication network, wherein the data packet contains information relating to at least one physical characteristic of the aerosol provision device. At 16-2, a data packet is received from a second aerosol provision device via a wireless communication network, wherein the data packet contains information relating to at least one physical characteristic of the second aerosol provision device. At 16-3, the identity of the first second aerosol provision device is determined based at least in part on the at least one physical characteristic of the first aerosol provision device. At 16-4, the identity of the second aerosol provision device is determined based at least in part on the at least one physical characteristic of the second aerosol provision device. At 16-5, an aspect of a user interface is changed based on the determined identity of the first and second aerosol provision device such as to enable a selection from a user of one of the first or second aerosol provision devices. This provides a simple means of identifying the aerosol provision device when first communicating with it.

The order of the steps of the method illustrated in FIG. 16 is only to provide an indication of the method and the steps may be performed in a different order. For example, determining the identity of the first aerosol provision device at S16-3 may occur before a data packet is received from a second aerosol provision device at S16-2. The method illustrated in FIG. 16 may also be extended to include more than two aerosol provision devices, such as 3, 5, 10 or more aerosol provision devices.

By displaying the representations and/or associated text for the two devices, as discussed above with respect to FIGS. 15 and 16, an intuitive approach is provided by which a user may be provided with information that permits identification of one from multiple aerosol provision devices prior to pairing with one of the devices. Such an approach to identity disambiguation provides a system that can reduce an error rate of pairing device selection and/or reduce the time taken to achieve a successful pairing. The user may be able to customize how the processor 64 of the portable electronic device 6 changes an aspect of the user interface or which aspect of the user interface the processor 64 based on the determined identity of the aerosol provision device. For example, the user may specify that only the shape of the aerosol provision device should be conveyed in the graphical representation, and the remaining information, such as color, UUID and product ID, should be displayed as text near the graphical representation. This may be particularly applicable if the user is color blind or unable to distinguish between the graphical representations which indicate the aerosol provision devices and the physical aerosol provision devices by color alone.

Therefore, from one perspective, there has been described a method and a portable electronic device. The method comprises receiving, via a wireless communication interface capable of supporting paired interaction, a data packet from an aerosol provision device via a wireless communication network. The data packet contains information relating to at least one physical characteristic of the aerosol provision device. An identity of the aerosol provision device is determined based at least in part on the at least one physical characteristic of the aerosol provision device and an aspect of a user interface is changed based on the determined identity of the aerosol provision device.

It should be appreciated that although the embodiments described above have been primarily described in relation to a wireless communication interface that uses Bluetooth LE, the principles of the present disclosure are not limited to using a particular wireless communication interface. For example, other implementations may be based on a Wi-Fi direct communication interface, or any other radio communication interface.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the disclosure scope defined by the claims or limitations on equivalents to the claims, and that other embodiments may be utilized and modifications may be made without departing from the scope and/or spirit of the claims.

Further examples consistent with the present teachings are set out in the following numbered clauses:

1. A method comprising:
   receiving, via a wireless communication interface capable of supporting paired interaction, a data packet from an aerosol provision device via a wireless communication network, wherein the data packet contains information relating to at least one physical characteristic of the aerosol provision device;
   determining an identity of the aerosol provision device based at least in part on the at least one physical characteristic of the aerosol provision device; and
   changing an aspect of a user interface based on the determined identity of the aerosol provision device.

The method of clause 1, wherein the wireless communication interface is a Bluetooth low energy communication interface.

The method of clause 2, wherein the data packet is a Bluetooth low energy data packet and the information relating to at least one physical characteristic of first and second aerosol provision device is contained within a packet data unit of the Bluetooth low energy data packet.

The method of any one of clauses 1 to 3, wherein the at least one physical characteristic comprises the color of the aerosol provision device.

The method of clause 4, wherein the color of the aerosol provision device is conveyed as a hex color code.

The method of clause 4, wherein the color of the aerosol provision device is conveyed as a predetermined code.

The method of clause 6, wherein determining the identity of the aerosol provision device comprises using information stored in a database in a memory to translate the predetermined code received in the data packet into a color of the aerosol provision device.

The method of any one of clauses 1 to 7, wherein the at least one physical characteristic comprises one or more of the shape of the aerosol provision device, the size of the aerosol provision device, the type of aerosol provision device.

The method of any one of clauses 1 to 8, wherein the data packet received from the aerosol provision device includes at least one of a batch number, a serial number and a product identification number of the aerosol provision device.

The method of any one of clauses 1 to 9, wherein determining the identity of the aerosol provision device comprises comparing the at least one physical characteristic of the aerosol provision device to a database of physical characteristics of aerosol provision devices stored in a memory.

The method of claim any one of clauses 1 to 10, wherein changing an aspect of the user interface comprises one or more of displaying a graphical representation of the aerosol provision device on the user interface, playing a video, playing a sound, changing one or more display settings of the user interface, and changing one or more colors displayed on the user interface.

The method of any one of clauses 1 to 11, further comprising:
receiving, via the wireless communication interface, a data packet from a second aerosol provision device via the wireless communication network, wherein the data packet contains information relating to at least one physical characteristic of the second aerosol provision device;
determining the identity of the second aerosol provision device based at least in part on the at least one physical characteristic of the second aerosol provision device; and
changing an aspect of a user interface based on the determined identity of the first and second aerosol provision device such as to enable a selection from a user of one of the first or second aerosol provision devices.

The method of clause 12, wherein changing an aspect of the user interface comprises displaying a first graphical representation which indicates the first aerosol provision device on a first portion of the user interface and a second graphical representation which indicates the second aerosol provision device on a second portion of the user interface.

A portable electronic device comprising:
at least one processor;
a wireless communication interface capable of supporting paired interaction;
memory comprising instructions which, when executed by the at least one processor cause the at least one processor to perform the method of any one of clauses 1 to 13.

Various embodiments of the claimed scope may suitably comprise, consist of, or consist essentially of, appropriate combinations of the disclosed elements, components, features, parts, steps, means, etc., other than those specifically described herein. In addition, this disclosure may include other concepts not presently claimed, but which may be claimed in future either in combination with or separately to the presently claimed features.

The invention claimed is:

1. A method comprising:
receiving, at a mobile phone via a Bluetooth protocol, and via a wireless communication interface capable of supporting paired interaction, a data packet from a first aerosol provision device via a wireless communication network, wherein the data packet contains information relating to at least one physical characteristic of the first aerosol provision device;
determining an identity of the first aerosol provision device based at least in part on information from the data packet; and
changing an aspect of a user interface on a display of the mobile phone based on the determined identity of the first aerosol provision device, wherein changing an aspect of the user interface comprises:
displaying a graphical representation of the first aerosol provision device on a first portion of the user interface, wherein the graphical representation includes a shape of the first aerosol provision device; and
wherein the method further comprises:
displaying information relating to an identity of a second aerosol provision device on a second portion of the user interface which comprises displaying a graphical representation of the second aerosol provision device that includes a shape of the second aerosol provision device on the second portion of the user interface.

2. The method of claim 1, wherein following determining the identity of the first aerosol provision device, the method further comprises allowing a user to block an operation of the first aerosol provision device.

3. The method of claim 1, wherein following determining the identity of the first_aerosol provision device, the method further comprises allowing a user to request commencement of a pairing process between the mobile phone and the first_aerosol provision device.

4. The method of claim 1, wherein the information relating to the identity of the second aerosol provision device on the second portion of the user interface is displayed in response to a user selecting the second aerosol provision device.

5. The method of claim 1, wherein the at least one physical characteristic comprises a color of the first aerosol provision device.

6. The method of claim 1, wherein the at least one physical characteristic comprises one or more of the shape of the first aerosol provision device, a size of the first aerosol provision device, or a type of first aerosol provision device.

7. The method of claim 1, wherein the data packet received from the first aerosol provision device includes at least one of a batch number, a serial number, or a product identification number of the first aerosol provision device.

8. The method of claim 1, wherein determining the identity of the first aerosol provision device comprises comparing the at least one physical characteristic of the first aerosol provision device to a database of physical characteristics of aerosol provision devices stored in a memory.

9. The method of claim 1, wherein changing the aspect of the user interface further comprises one or more of playing a video, playing a sound, changing one or more display settings of the user interface, or changing one or more colors displayed on the user interface.

10. The method of claim 1, wherein determining the identity of the first aerosol provision device based at least in part on information from the data packet comprises determining the identity of the aerosol provision device based at least in part on the at least one physical characteristic of the first aerosol provision device.

11. A mobile phone comprising:

at least one processor;

a wireless communication interface capable of supporting paired interaction; and memory comprising instructions which, when executed by the at least one processor, cause the at least one processor to perform the method of claim 1.

* * * * *

UNITED STATES PATENT AND TRADEMARK OFFICE
CERTIFICATE OF CORRECTION

| | | |
|---|---|---|
| PATENT NO. | : 12,143,914 B2 | Page 1 of 1 |
| APPLICATION NO. | : 18/322834 | |
| DATED | : November 12, 2024 | |
| INVENTOR(S) | : Darryl Baker et al. | |

It is certified that error appears in the above-identified patent and that said Letters Patent is hereby corrected as shown below:

In the Claims

In Column 22, Claim 3, Line 46, "first_aerosol provision device" should read -- first aerosol provision device --

In Column 22, Claim 3, Line 49, "first_aerosol provision device" should read -- first aerosol provision device --

Signed and Sealed this
First Day of April, 2025

Coke Morgan Stewart
*Acting Director of the United States Patent and Trademark Office*